United States Patent [19]

Panzeri et al.

[11] Patent Number: 5,155,107

[45] Date of Patent: Oct. 13, 1992

[54] 17β-SUBSTITUTED-4-AZA-5α-ANDROSTAN-3-ONE DERIVATIVES AND PROCESS FOR THEIR PREPARATION

[75] Inventors: Achille Panzeri, Merate; Enrico Di Salle; Marcella Nesi, both of Milan, all of Italy

[73] Assignee: Farmitalia Carlo Erba, Milan, Italy

[21] Appl. No.: 650,970

[22] Filed: Feb. 5, 1991

[30] Foreign Application Priority Data

Feb. 9, 1990 [GB] United Kingdom ............... 9002922

[51] Int. Cl.$^5$ ................... C07J 73/00; A61K 31/56; A61K 31/58
[52] U.S. Cl. .................... 514/232.8; 514/255; 514/284; 544/125; 544/361; 546/77
[58] Field of Search ............. 544/125, 361; 546/77; 514/255, 232.8, 284; 552/610, 611

[56] References Cited

U.S. PATENT DOCUMENTS

| | | |
|---|---|---|
| 4,220,775 | 9/1980 | Rasmusson et al. ............... 546/77 |
| 4,317,817 | 3/1982 | Blohm et al. ............... 552/505 |
| 4,377,584 | 3/1983 | Rasmusson et al. ............... 514/284 |
| 4,396,615 | 8/1983 | Petrow et al. ............... 552/529 |

FOREIGN PATENT DOCUMENTS

| | | | |
|---|---|---|---|
| 970692 | 7/1975 | Canada ............... | 552/610 |
| 4949 | 4/1978 | European Pat. Off. ............... | 546/77 |
| 200859 | 3/1985 | European Pat. Off. ............... | 546/77 |
| 155096 | 9/1985 | European Pat. Off. ............... | 546/77 |
| 271220 | 11/1986 | European Pat. Off. ............... | 546/77 |
| 298652 | 1/1989 | European Pat. Off. ............... | 552/505 |

OTHER PUBLICATIONS

Kedderis et al. Chemical Abstracts, vol. 112, 1990, Abstract 70208d.
The Journal of Biological Chemistry, vol. 243, No. 22, Issue of Nov. 25, 1968, pp. 5953–5960.
The Journal of Clinical Investigation, vol. 49, Mar. 6, 1970, pp. 1737–1753.
Arch Dermatol vol. 111, Nov. 1975, pp. 1496–1502, Testerone Metabolism in the Skin.
Supplement to Urology, Apr. 1981, vol. 17, No. 4, Avery A. Sandberg, M.D. pp. 34–44.
Endo, vol. 92, pp. 1216–1222 (1973) Walter Voigt and S. L. Hsia.
Journal of Steroid Biochemistry, vol. 3, pp. 307–310, (1977) B. Robaire et al.
Steroids, vol. 38, No. 2, Aug., 1981 Vladimir Petrow et al., pp. 121–140.
Biochemical and Biophysical research Communications, pp. 273–280, vol. 95, No. 1, 1980 Jul. 16, 1980.
J. Steroid Biochem, vol. 19, No. 1, pp. 385–390, 1983, Tehming Liang et al.
Eur. J. Med. Chem. vol. 24, pp. 421–426 (1989) Enzo Brambilla et al.
Chemical Review, vol. 43, pp. 203–218 (1948) J. H. Saunders et al.
Chemical Review, vol. 57, pp. 49–54 (1957) R. G. Arnold et al.
Chemical Review, vol. 53, pp. 145–146, 154–157, (1953) H. G. Khorana.
Chemical Review, vol. 67, No. 2, pp. 123–127 (1967) Frederick Kurzer et al.
J. Org. Chem. 1965, vol. 30, pp. 2849–2851 Zoltan G. Hajos et al.
Chem. Ber. vol., 72, pp. 1735–1740 (1939).
JACS, vol. 70, (1948) pp. 2427–2428 A. L. Wilds et al.
Helv. Chem. Acta, vol. 37, (1954) pp. 45–58 F. Reber et al.
Can J. Chem., vol. 33, (1955) pp. 1515–1520 R. Engel et al.
Angew. Chem, vol. 74, pp. 407–423, (1962) Von. Prof. Dr. H. A. Staab.
Tetrahedron, vol. 33, pp. 683–710, (1977) K. C. Nocolaou.
JACS, vol. 86, (1963) pp. 1839–1842, George W. Anderson et al.
Z. Naturforschg. 21.b, (1966) vol. 21, pp. 426–428 Friedrich Weygand et al.
Communications to the Editor, (1961) p. 1263. J.A.C.S.
Chem. Ber. vol. 103, pp. 788–798 (1970) Konig et al.
Communications, (1985) pp. 671–672, Yoshio Kobayashi et al. Synthesis.
Thiocarbonsauren, pp. 832–842, Dr. Wolfgang Bauer et al. Houben Weyl E5 (1976).
Comprehensive Organic Chemistry, vol. 3, pp. 420–432, (1989).
J. Med. Chem, vol. 27, (1984) pp. 1690–1701 Gary H. Rasmusson et al.
J. Med. Chem. vol. 29, (1986) pp. 2298–2315, Gary H. Rasmusson et al.

*Primary Examiner*—Robert T. Bond
*Assistant Examiner*—E. C. Ward
*Attorney, Agent, or Firm*—Oblon, Spivak, McClelland, Maier & Neustadt

[57] ABSTRACT

The present invention concerns steroidic 5α-reductase inhibitors having the formula:

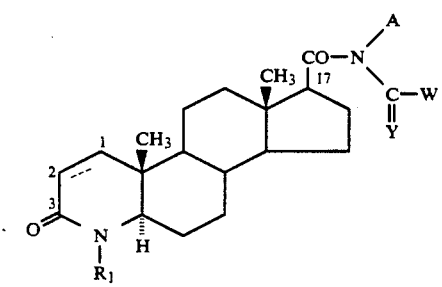

As a result of their 5α-reductase inhibiting activity, these compounds are useful in the treatment of androgen dependent conditions and diseases.

7 Claims, No Drawings

17β-SUBSTITUTED-4-AZA-5α-ANDROSTAN-3-ONE DERIVATIVES AND PROCESS FOR THEIR PREPARATION

The present invention relates to new 17β-substituted-4-aza-5α-androstan-3-one derivatives, to a process for their preparation, to pharmaceutical compositions containing them and to the use of said compounds as inhibitors of androgen action, by means of testosterone 5α-reductase inhibition. In certain androgen responsive tissues the action of testosterone is mediated primarily through its 5α-reduced metabolite, dihydrotestosterone (DHT) (Bruchowsky N., Wilson J. D.; J. Biol. Chem. 243, 5953, 1968). The conversion of testosterone to dihydrotestosterone is catalyzed by the enzyme 5α-reductase and if 5α-reductase is inhibited, the formation of dihydrotestosterone is reduced and its specific androgenic effect is attenuated or prevented.

The 5α-reductase inhibitors may find medical application for the treatment of hyperandrogenic conditions, e.g. certain prostatic diseases, such as benign prostatic hyperplasia and prostatic cancer, and certain skin-hair conditions, such as acne, seborrhoea, female hirsutism and male pattern baldness (Siiteri P. K., Wilson J. D., J. Clin. Invest. 49, 1737, 1970; Price V. H., Arch. Dermatol. III, 1496, 1975; Sandberg A. A., Urology 17, 34, 1981). Also breast cancer treatment can take advantage from use of 5α-reductase inhibitors as the said tumor is known to be aggravated by presence of androgens.

Androst-4-en-3-one-17β-carboxylic acid and its methyl ester (Voigt and Hsia, Endocrinology, 92, 1216 (1973); Canadian Patent No. 970,692) are among the first steroidic compounds described as 5α-reductase inhibitors.

Two 5,10-secosteroids having a 3-keto-4,5-diene system in the expanded ring have been found to be selective inhibitors of rat epididymal 5α-reductase (Robaire et al., J. Steroid Biochem. 8, 307–310 (1977)).

The (20R)-4-diazo-21-hydroxy-20-methyl-5α-pregnan-3-one and its analogs are reported to be enzyme activated inhibitors of testosterone 5α-reductase (Blohm et al., Biochem. Biophys. Res. Comm. 95, 273–80 (1980); U.S. Pat. No. 4,317,817).

Another series of enzyme-directed irreversible inhibitors of 5α-reductase have been prepared by introducing a 6-methylene moiety into substrates type 3-keto-$\Delta^4$-progestins and androgens (Petrow et al., Steroids 38, 352–53 (1981); U.S. Pat. No. 4,396,615)).

More recently 4-aza-steroids have also been reported as inhibitors of steroid 5α-reductase (Liang et al., J. Steroid. Biochem. 19, 385–90 (1983); U.S. Pat. No. 4,377,584 and published European Patent Application no. 155,096).

We have found a new group of 4-aza-steroid derivatives with testosterone 5α-reductase-inhibiting properties.

Accordingly the present invention provides novel 17β-substituted-4-aza-5α-androstan-3-one derivatives of the following formula (I):

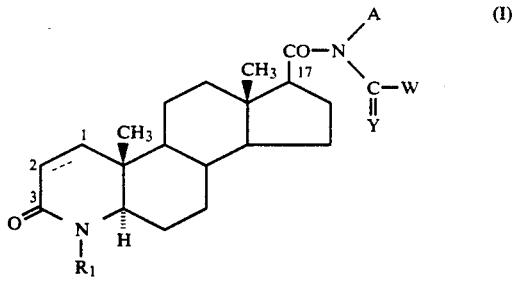

wherein:
$R_1$ is hydrogen, a $C_1$–$C_6$ alkyl group, an aryl-$C_1$–$C_6$alkyl group, or an aroyl group;
Y is oxygen or sulphur;
W is a group

wherein each of $R_2$ and $R_3$ is independently selected from the group consisting of hydrogen, $C_1$–$C_6$ alkyl, $C_5$–$C_6$ cycloalkyl, $C_6$–$C_9$ cycloalkylalkyl and aryl, wherein each of the groups alkyl, cycloalkyl, cycloalkylalkyl and aryl may be unsubstituted or substituted by a substituent —$OR_4$ wherein $R_4$ is hydrogen or $C_1$–$C_4$ alkyl;

A is hydrogen, $C_1$–$C_6$ alkyl, $C_5$–$C_6$ cycloalkyl or $C_6$–$C_9$ cycloalkylalkyl wherein each of the groups alkyl, cycloalkyl and cycloalkylalkyl, may be unsubstituted or substituted by a substituent chosen from:
a) —$OR_4$ wherein $R_4$ is as defined above, and
b)

wherein either each of $R_5$ and $R_6$ is independently selected from the group consisting of hydrogen, $C_1$–$C_6$ alkyl, $C_5$–$C_6$ cycloalkyl and aryl, or $R_5$ and $R_6$, taken together with the nitrogen atom to which they are linked, form a pentatomic or hexatomic saturated heteromonocyclic ring, optionally containing at least one additional heteroatom selected from oxygen and nitrogen; and the symbol (≡) represents a single or a double bond. In the formulae of this specification the dotted line (''''''') indicates a substituent in the α configuration, i.e. below the plane of the ring, and the wedged line (◀) indicates a substituent in the β configuration, i.e. above the plane of the ring.

The invention includes also the pharmaceutically acceptable salts of the compounds of formula (I) as well as all the possible isomers of formula (I) and their mixtures.

Also the metabolites and the metabolic precursors of the compounds of formula (I) are within the scope of the present invention.

In this specification the alkyl groups and the aliphatic portions of the arylalkyl and cycloalkylalkyl groups may be straight or branched chain.

A C$_1$-C$_5$ alkyl group may be, for example, methyl, ethyl, isopropyl, n-butyl, tert-butyl or tert-butylmethyl (i.e. neopentyl).

A C$_1$-C$_4$ alkyl group is, preferably, methyl or ethyl.

An aryl C$_1$-C$_6$ alkyl group is, preferably a benzyl group wherein the aromatic moiety may be optionally substituted, e.g. by a C$_1$-C$_6$ alkoxy group, in particular methoxy or ethoxy.

An aroyl group is, preferably, benzoyl.

A C$_5$-C$_6$ cycloalkyl group is cyclopentyl or cyclohexyl, preferably cyclohexyl.

A C$_6$-C$_9$ cycloalkylalkyl group may be, for example, cyclohexylmethyl.

An aryl group is, preferably, phenyl.

When R$_1$ is C$_1$-C$_6$ alkyl, it is, preferably, methyl or ethyl, most preferably methyl.

When R$_1$ is aryl —C$_1$-C$_6$ alkyl, it is preferably benzyl or p-methoxybenzyl.

When R$_1$ is aroyl, it is preferably benzoyl.

Preferably R$_1$ is hydrogen or C$_1$-C$_6$ alkyl, in particular methyl.

When W is a group

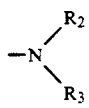

as defined above, preferably each of R$_2$ and R$_3$ is, independently, hydrogen, C$_1$-C$_6$ alkyl, cyclohexyl, cyclohexylmethyl or phenyl.

When A is C$_1$-C$_6$ alkyl, it is, preferably C$_1$-C$_5$ alkyl, for example methyl, ethyl, isopropyl, n-butyl, tert-butyl or tert-butylmethyl.

When A is C$_5$-C$_6$ cycloalkyl, it is preferably cyclohexyl.

When A is C$_6$-C$_9$ cycloalkylalkyl, it is, preferably cyclohexylmethyl.

When A is a C$_1$-C$_6$ alkyl, C$_5$-C$_6$ cycloalkyl or C$_6$-C$_9$ cycloalkylalkyl group substituted by a group —OR$_4$, the group —OR$_4$ is, preferably, methoxy or ethoxy; when A is a C$_1$-C$_6$ alkyl, C$_5$-C$_6$ cycloalkyl or C$_6$-C$_9$ cycloalkylalkyl group substituted by a group

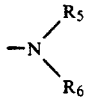

as defined above, the group

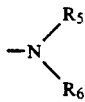

is, preferably, dimethylamino or diethylamino.

When in the group

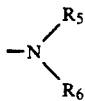

R$_5$ and R$_6$ taken together with the nitrogen atom to which they are linked, form a pentatomic or hexatomic saturated heteromonocyclic ring as defined above, the group

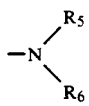

is, preferably

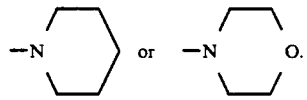

Pharmaceutically acceptable salts of the compounds of the invention are salts with pharmaceutically acceptable acids, either inorganic acids, such as, e.g., hydrochloric, sulfuric, phosphoric, hydrobromic or nitric acid, or organic acids, such as, for instance, acetic, formic, propionic, benzoic, maleic, malic, fumaric, succinic, tartaric, citric, oxalic, methanesulphonic, ethanesulphonic or p-toluensulphonic acid.

A preferred class of compounds according to the invention are the compounds of formula (I) wherein:
R$_1$ is hydrogen or C$_1$-C$_6$ alkyl;
Y is oxygen or sulphur;
W is

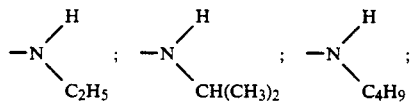

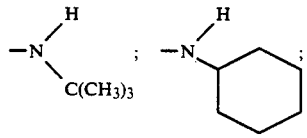

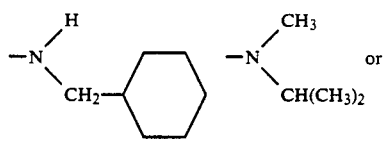

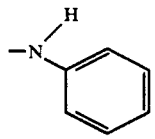

A is hydrogen, methyl, —CH(CH$_3$)$_2$, —C(CH$_3$)$_3$, —CH$_2$C(CH$_3$)$_3$,

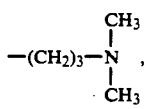

—(CH$_2$)$_3$OCH$_2$CH$_3$; cyclohexyl; or cyclohexyl methyl; the symbol ⇌ represents a single or double bond, and the pharmaceutically acceptable salts thereof.

In the above preferred class when R$_1$ is C$_1$-C$_6$ alkyl, it is more preferably methyl.

Examples of specific compounds preferred under this invention are:
1) 4-methyl-17β-[N-isopropyl-N-(N-isopropylcarbamoyl) carbamoyl]-4-aza-5α-androstan-3-one;

2) 4-methyl-17β-[N-isopropyl-N-(N-methyl-N-isopropylcarbamoyl)carbamoyl]-4-aza-5α-androstan-3-one;
3) 17β-[N-isopropyl-N-(N-isopropylcarbamoyl)carbamoyl]-4-aza-5α-androstan-3-one;
4) 4-methyl-17β-[N-isopropyl-N-(N-isopropylcarbamoyl) carbamoyl]-4-aza-5α-androst-1-en-3-one;
5) 17β-[N-isopropyl-N-(N-isopropylcarbamoyl)carbamoyl]-4-aza-5α-androst-1-en-3-one;
6) 17β-[N-isopropyl-N-(N-methyl-N-isopropylcarbamoyl) carbamoyl]-4-aza-5α-androst-1-en-3-one;
7) 4-methyl-17β-[N-tert-butyl-N-(N-tert-butylcarbamoyl) carbamoyl]-4-aza-5α-androstan-3-one;
8) 17β-[N-tert-butyl-N-(N-tert-butylcarbamoyl) carbamoyl]-4-aza-5α-androstan-3-one;
9) 4-methyl-17β-[N-tert-butyl-N-(N-tert-butylcarbamoyl) carbamoyl]-4-aza-5α-androst-1-en-3-one;
10) 17β-[N-tert-butyl-N-(N-tert-butylcarbamoyl)carbamoyl]-4-aza-5α-androst-1-en-3-one;
11) 4-methyl-17β-[N-cyclohexyl-N-(N-cyclohexylcarbamoyl) carbamoyl]-4-aza-5α-androstan-3-one;
12) 17β-[N-cyclohexyl-N-(N-cyclohexylcarbamoyl)-carbamoyl]-4-aza-5α-androstan-3-one;
13) 4-methyl-17β-[N-cyclohexyl-N-(N-cyclohexylcarbamoyl) carbamoyl]-4-aza-5α-androst-1-en-3-one;
14) 17β-[N-cyclohexyl-N-(N-cyclohexylcarbamoyl)carbamoyl]-4-aza-5α-androst-1-en-3-one;
15) 4-methyl-17β-[N-(N-tert-butylcarbamoyl)carbamoyl]-4-aza-5α-androstan-3-one;
16) 17β-[N-(N-tert-butylcarbamoyl)carbamoyl]-4-aza-5α-androstan-3-one;
17) 4-methyl-17β-[N-(N-tert-butylcarbamoyl)carbamoyl]-4-aza-5α-androst-1-en-3-one;
18) 17β-[N-(N-tert-butylcarbamoyl)carbamoyl]-4-aza-5α-androst-1-en-3-one;
19) 4-methyl-17β-[N-(N-butylcarbamoyl)carbamoyl]-4-aza-5α-androstan-3-one;
20) 17β-[N-[N-butylcarbamoyl)carbamoyl]-4-aza-5α-androstan-3-one;
21) 4-methyl-17β-[N-(N-butylcarbamoyl)carbamoyl]-4-aza-5α-androst-1-en-3-one;
22) 17β-[N-(N-butylcarbamoyl)carbamoyl]-4-aza-5α-androst-1-en-3-one;
23) 4-methyl-17β-[N-neopentyl-N-(N-ethylcarbamoyl)-carbamoyl]-4-aza-5α-androstan-3-one;
24) 17β-[N-neopentyl-N-(N-ethylcarbamoyl)carbamoyl]-4-aza-5α-androstan-3-one;
25) 4-methyl-17β-[N-neopentyl-N-(N-ethylcarbamoyl)-carbamoyl]-4-aza-5α-androst-1-en-3-one;
26) 17β-[N-neopentyl-N-(N-ethylcarbamoyl)carbamoyl]-4-aza-5α-androst-1-en-3-one;
27) 4-methyl-17β-{N-[3-(dimethylamino)-propyl]-N-(N-ethylcarbamoyl)carbamoyl}-4-aza-5α-androstan-3-one hydrochloride;
28) 17β-{N-[3-(dimethylamino)propyl]-N-(N-ethylcarbamoyl) carbamoyl}-4-aza-5α-androstan-3-one hydrochloride;
29) 4-methyl-17β-{N-[3-(dimethylamino)propyl]-N-(N-ethylcarbamoyl)}carbamoyl-4-aza-5α-androst-1-en-3-one hydrochloride;
30) 17β-{N-[3-(dimethylamino)propyl]-N-(N-ethylcarbamoyl) carbamoyl}-4-aza-5α-androst-1-en-3-one hydrochloride;
31) 4-methyl-17β-[N-(3-ethoxy-propyl)-N-(N-ethylcarbamoyl) carbamoyl]-4-aza-5α-androstan-3-one;
32) 17β-[N-(3-ethoxy-propyl)-N-[N-ethylcarbamoyl]carbamoyl]-4-aza-5α-androstan-3-one;
33) 4-methyl-17β-[N-(3-ethoxy-propyl)-N-(N-ethylcarbamoyl) carbamoyl]-4-aza-5α-androst-1-en-3-one;
34) 17β-[N-(3-ethoxy-1-propyl)-N-(N-ethylcarbamoyl) carbamoyl]-4-aza-5α-androst-1-en-3-one;
35) 4-methyl-17β-[N-cyclohexylmethyl-N-(N-cyclohexylmethylcarbamoyl)carbamoyl]-4-aza-5α-androstan-3-one;
36) 17β-[N-cyclohexylmethyl-N-(N-cyclohexylmethylcarbamoyl) carbamoyl]-4-aza-5α-androst-1-en-3-one;
37) 4-methyl-17β-[N-isopropyl-N-(N-phenylcarbamoyl)carbamoyl]-4-aza-5α-androst-1-en-3-one;
38) 4-methyl-17β-[N-methyl-N-(N-tert-butylcarbamoyl) carbamoyl]-4-aza-5α-androstan-3-one;
39) 4-methyl-17β-[N-isopropyl-N-(N-isopropylthiocarbamoyl) carbamoyl]-4-aza-5α-androstan-3-one;
40) 4-methyl-17β-[N-isopropyl-N-(N-methyl-N-isopropylthiocarbamoyl)carbamoyl]-4-aza-5α-androstan-3-one;
41) 17β-[N-isopropyl-N-(N-isopropylthiocarbamoyl)-carbamoyl]-4-aza-5α-androstan-3-one;
42) 4-methyl-17β-[N-isopropyl-N-(N-isopropylthiocarbamoyl) carbamoyl]-4-aza-5α-androst-1-en-3-one;
43) 17β-[N-isopropyl-N-(N-isopropylthiocarbamoyl)-carbamoyl]-4-aza-5α-androst-1-en-3-one;
44) 17β-[N-isopropyl-N-(N-methyl-N-isopropylthiocarbamoyl) carbamoyl]-4-aza-5α-androst-1-en-3-one;
45) 4-methyl-17β-[N-tert-butyl-N-(N-tert-butylthiocarbamoyl) carbamoyl]-4-aza-5α-androstan-3-one;
46) 17β-[N-tert-butyl-N-(N-tert-butylthiocarbamoyl)-carbamoyl]-4-aza-5α-androstan-3-one;
47) 4-methyl-17β-[N-tert-butyl-N-(N-tert-butylthiocarbamoyl) carbamoyl]-4-aza-5α-androst-1-en-3-one;
48) 17β-[N-tert-butyl-N-(N-tert-butylthiocarbamoyl)-carbamoyl]-4-aza-5α-androst-1-en-3-one;
49) 4-methyl-17β-[N-cyclohexyl-N-[N-cyclohexylthiocarbamoyl) carbamoyl]-4-aza-5α-androstan-3-one;
50) 17β-[N-cyclohexyl-N-(N-cyclohexylthiocarbamoyl)carbamoyl]-4-aza-5α-androstan-3-one;
51) 4-methyl-17β-[N-cyclohexyl-N-(N-cyclohexylthiocarbamoyl) carbamoyl]-4-aza-5α-androst-1-en-3-one;
52) 17β-[N-cyclohexyl-N-[N-cyclohexylthiocarbamoyl)carbamoyl]-4-aza-5α-androst-1-en-3-one;
53) 4-methyl-17β-[N-(N-tert-butylthiocarbamoyl)carbamoyl]-4-aza-5α-androstan-3-one;
54) 17β-[N-(N-tert-butylthiocarbamoyl)carbamoyl]-4-aza-5α-androstan-3-one;
55) 4-methyl-17β-[N-(N-tert-butylthiocarbamoyl)carbamoyl]-4-aza-5α-androst-1-en-3-one;
56) 17β-[N-(N-tert-butylthiocarbamoyl)carbamoyl]-4-aza-5α-androst-1-en-3-one;
57) 4-methyl-17β-[N-(N-butylthiocarbamoyl)carbamoyl]-4-aza-5α-androstan-3-one;
58) 17β-[N-(N-butylthiocarbamoyl)carbamoyl]-4-aza-5αandrostan-3-one;
59) 4-methyl-17β-[N-(N-butylthiocarbamoyl)carbamoyl]-4-aza-5α-androst-1-en-3-one;
60) 17β-[N-(N-butylthiocarbamoyl)carbamoyl]-4-aza-5α-androst-1-en-3-one;
61) 4-methyl-17β-[N-neopentyl-N-(N-ethylthiocarbamoyl) carbamoyl]-4-aza-5α-androstan-3-one;
62) 17β-[N-neopentyl-N-(N-ethylthiocarbamoyl)carbamoyl]-4-aza-5α-androstan-3-one;
63) 4-methyl-17β-[N-neopentyl-N-(N-ethylthiocarbamoyl) carbamoyl]-4-aza-5α-androst-1-en-3-one;
64) 17β-[N-neopentyl-N-(N-ethylthiocarbamoyl)carbamoyl]-4-aza-5α-androst-1-en-3-one;

65) 4-methyl-17β-{N-[3-[dimethylamino)-propyl]-N-(N-ethylthiocarbamoyl)carbamoyl}-4-aza-5α-androstan-3-one hydrochloride;
66) 17β-{N-[3-(dimethylamino)propyl]-N-(N-ethylthiocarbamoyl)carbamoyl}-4-aza-5α-androstan-3-one hydrochloride;
67) 4-methyl-17β-{N-[3-(dimethylamino)propyl]-N-(N-ethylthiocarbamoyl)}carbamoyl-4-aza-5α-androst-1-en-3-one hydrochloride;
68) 17β-{N-[3-(dimethylamino)propyl]-N-(N-ethylthiocarbamoyl)carbamoyl}-4-aza-5α-androst-1-en-3-one hydrochloride;
69) 4-methyl-17β-[N-(3-ethoxy-propyl)-N-(N-ethylthiocarbamoyl) carbamoyl]-4-aza-5α-androstan-3-one;
70) 17β-[N-(3-ethoxy-propyl)-N-(N-ethylthiocarbamoyl) carbamoyl]-4-aza-5α-androstan-3-one;
71) 4-methyl-17β-[N-(3-ethoxy-propyl)-N-(N-ethylthio carbamoyl)carbamoyl]-4-aza-5α-androst-1-en-3-one;
72) 17β-[N-(3-ethoxy-1-propyl)-N-(N-ethylthiocarbamoyl) carbamoyl]-4-aza-5α-androst-1-en-3-one;
73) 4-methyl-17β-[N-cyclohexylmethyl-N-(N-cyclohexylmethylthiocarbamoyl)carbamoyl]-4-aza-5α-androstan-3-one;
74) 17β-[N-cyclohexylmethyl-N-(N-cyclohexylmethylthio carbamoyl)carbamoyl]-4-aza-5α-androst-1-en-3-one;
75) 4-methyl-17β-[N-isopropyl-N-(N-phenylthiocarbamoyl) carbamoyl]-4-aza-5α-androst-1-en-3-one;
76) 4-methyl-17β-[N-methyl-N-(N-tert-butylthiocarbamoyl) carbamoyl]-4-aza-5α-androstan-3-one, and the pharmaceutically acceptable salts thereof.

The structural formulae of the above listed compounds, according to their progressive number, are tabulated below with reference to the formula (I) substituents:

| | Bond | Y | $R_1$ | A | W |
|---|---|---|---|---|---|
| 1 | single | O | $CH_3$ | iPr | NH-iPr |
| 2 | single | O | $CH_3$ | iPr | $N(CH_3)$iPr |
| 3 | single | O | H | iPr | NH-iPr |
| 4 | double | O | $CH_3$ | iPr | NH-iPr |
| 5 | double | O | H | iPr | NH-iPr |
| 6 | double | O | H | iPr | $N(CH_3)$iPr |
| 7 | single | O | $CH_3$ | tBu | NH-tBu |
| 8 | single | O | H | tBu | NH-tBu |
| 9 | double | O | $CH_3$ | tBu | NH-tBu |
| 10 | double | O | H | tBu | NH-tBu |
| 11 | single | O | $CH_3$ | 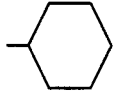 | 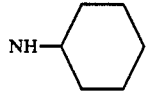 |
| 12 | single | O | H | 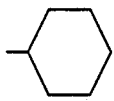 | 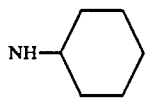 |
| 13 | double | O | $CH_3$ | 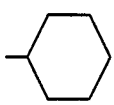 | 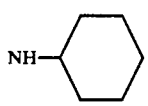 |
| 14 | double | O | H | 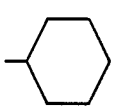 | 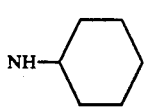 |
| 15 | single | O | $CH_3$ | H | NH-tBu |
| 16 | single | O | H | H | NH-tBu |
| 17 | double | O | $CH_3$ | H | NH-tBu |
| 18 | double | O | H | H | NH-tBu |
| 19 | single | O | $CH_3$ | H | NH—Bu |
| 20 | single | O | H | H | NH—Bu |
| 21 | double | O | $CH_3$ | H | NH—Bu |
| 22 | double | O | H | H | NH—Bu |
| 23 | single | O | $CH_3$ | $CH_2-C(CH_3)_3$ | $NH-CH_2-CH_3$ |
| 24 | single | O | H | $CH_2-C(CH_3)_3$ | $NH-CH_2-CH_3$ |
| 25 | double | O | $CH_3$ | $CH_2-C(CH_3)_3$ | $NH-CH_2-CH_3$ |
| 26 | double | O | H | $CH_2-C(CH_3)_3$ | $NH-CH_2-CH_3$ |
| 27 | single | O | $CH_3$ | 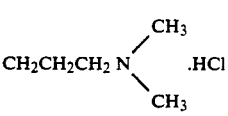 | $NH-CH_2CH_3$ |

-continued

| | Bond | Y | R₁ | A | W |
|---|---|---|---|---|---|
| 28 | single | O | H | CH₂CH₂CH₂N(CH₃)(CH₃)·HCl | NH—CH₂CH₃ |
| 29 | double | O | CH₃ | CH₂CH₂CH₂N(CH₃)(CH₃)·HCl | NH—CH₂CH₃ |
| 30 | double | O | H | CH₂CH₂CH₂N(CH₃)(CH₃) | NH—CH₂CH₃ |
| 31 | single | O | CH₃ | CH₂CH₂CH₂OEt | NH—CH₂CH₃ |
| 32 | single | O | H | CH₂CH₂CH₂OEt | NH—CH₂CH₃ |
| 33 | double | O | CH₃ | CH₂CH₂CH₂OEt | NH—CH₂CH₃ |
| 34 | double | O | H | CH₂CH₂CH₂OEt | NH—CH₂CH₃ |
| 35 | single | O | CH₃ | CH₂-cyclohexyl | NH—CH₂-cyclohexyl |
| 36 | double | O | H | CH₂-cyclohexyl | NH—CH₂-cyclohexyl |
| 37 | double | O | CH₃ | iPr | NH-phenyl |
| 38 | single | O | CH₃ | CH₃ | NH-tBu |
| 39 | single | S | CH₃ | iPr | NH-iPr |
| 40 | single | S | CH₃ | iPr | N(CH₃)iPr |
| 41 | single | S | H | iPr | NH-iPr |
| 42 | double | S | CH₃ | iPr | NH-iPr |
| 43 | double | S | H | iPr | NH-iPr |
| 44 | double | S | H | iPr | N(CH₃)iPr |
| 45 | single | S | CH₃ | tBu | NH-tBu |
| 46 | single | S | H | tBu | NH-tBu |
| 47 | double | S | CH₃ | tBu | NH-tBu |
| 48 | double | S | H | tBu | NH-tBu |
| 49 | single | S | CH₃ | cyclohexyl | NH-cyclohexyl |
| 50 | single | S | H | cyclohexyl | NH-cyclohexyl |
| 51 | double | S | CH₃ | cyclohexyl | NH-cyclohexyl |
| 52 | double | S | H | cyclohexyl | NH-cyclohexyl |
| 53 | single | S | CH₃ | H | NH-tBu |
| 54 | single | S | H | H | NH-tBu |
| 55 | double | S | CH₃ | H | NH-tBu |
| 56 | double | S | H | H | NH-tBu |

-continued

| | Bond | Y | R₁ | A | W |
|---|---|---|---|---|---|
| 57 | single | S | CH₃ | H | NH—Bu |
| 58 | single | S | H | H | NH—Bu |
| 59 | double | S | CH₃ | H | NH—Bu |
| 60 | double | S | H | H | NH—Bu |
| 61 | single | S | CH₃ | CH₂—C(CH₃)₃ | NH—CH₂—CH₃ |
| 62 | single | S | H | CH₂—C(CH₃)₃ | NH—CH₂—CH₃ |
| 63 | double | S | CH₃ | CH₂—C(CH₃)₃ | NH—CH₂—CH₃ |
| 64 | double | S | H | CH₂—C(CH₃)₃ | NH—CH₂—CH₃ |
| 65 | single | S | CH₃ | CH₂CH₂CH₂N(CH₃)(CH₃) .HCl | NH—CH₂CH₃ |
| 66 | single | S | H | CH₂CH₂CH₂N(CH₃)(CH₃) .HCl | NH—CH₂CH₃ |
| 67 | double | S | CH₃ | CH₂CH₂CH₂N(CH₃)(CH₃) .HCl | NH—CH₂CH₃ |
| 68 | double | S | H | CH₂CH₂CH₂N(CH₃)(CH₃) | NH—CH₂CH₃ |
| 69 | single | S | CH₃ | CH₂CH₂CH₂OEt | NH—CH₂CH₃ |
| 70 | single | S | H | CH₂CH₂CH₂OEt | NH—CH₂CH₃ |
| 71 | double | S | CH₃ | CH₂CH₂CH₂OEt | NH—CH₂CH₃ |
| 72 | double | S | H | CH₂CH₂CH₂OEt | NH—CH₂CH₃ |
| 73 | single | S | CH₃ | CH₂-cyclohexyl | NH—CH₂-cyclohexyl |
| 74 | double | S | H | CH₂-cyclohexyl | NH—CH₂-cyclohexyl |
| 75 | double | S | CH₃ | iPr | NH—phenyl |
| 76 | single | S | CH₃ | CH₃ | NH-tBu |

The abbreviation iPr, Bu and tBu stand respectively for isopropyl, normal butyl and tertiar-butyl.

The compounds of formula (I) may be obtained by a process comprising:

1) reacting a compound of formula (II)

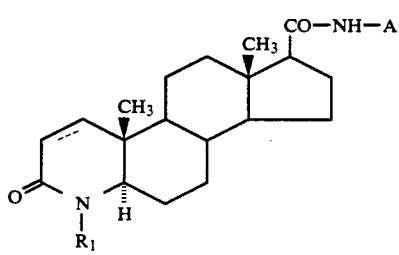

(II)

wherein: the symbol $=$, A and $R_1$ are as defined above, provided that $R_1$ does not represent hydrogen, with a compound of formula (III)

$$R_7—N=C=Y \qquad (III)$$

wherein Y is defined above and $R_7$ is $C_1$-$C_6$ alkyl, $C_5$-$C_6$ cycloalkyl, $C_6$-$C_9$ cycloalkylalkyl or aryl, so obtaining a compound of formula (I) wherein the symbol $=$, Y and A are as defined above and W is a

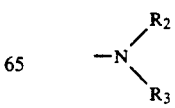

wherein one of $R_2$ and $R_3$ is hydrogen and the other is $C_1$-$C_6$ alkyl, $C_5$-$C_6$ cycloalkyl, $C_6$-$C_9$ cycloalkylalkyl or aryl; or 2) reacting a compound of formula (IV)

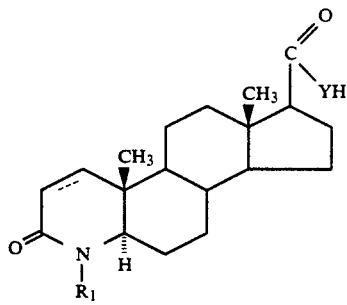
(IV)

wherein the symbol ═, Y and $R_1$ are as defined above, with a compound of formula (V)

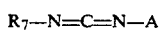
(V)

wherein $R_7$ and A are as defined above, so obtaining a compound of formula (I) wherein the symbol ═, Y, $R_1$ and A are as defined above, and W is a group

wherein one of $R_2$ and $R_3$ is hydrogen and the other is $C_1$-$C_6$ alkyl, $C_5$-$C_6$ cycloalkyl, $C_6$-$C_9$ cycloalkylalkyl or aryl; or 3) reacting a compound of formula (VI)

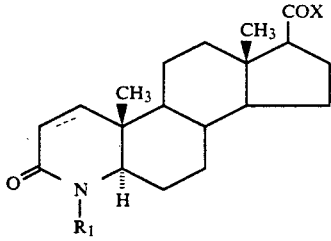
(VI)

wherein the symbol ═ and $R_1$ are as defined above and X is an activating group of the carboxylic function with a compound of formula (VII)

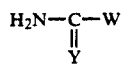
(VII)

wherein Y and W are as defined above, so obtaining a compound of formula (I) wherein the symbol ═, $R_1$, Y and W are as defined above and A is hydrogen; or 4) alkylating a compound of formula (I) wherein the symbol ═, $R_1$, Y and A are as defined above, provided that $R_1$ and A are different from hydrogen, W is a group

wherein one of $R_2$ and $R_3$ is hydrogen and the other is $C_1$-$C_6$ alkyl, $C_5$-$C_6$ cycloalkyl, $C_6$-$C_9$ cycloalkylalkyl or aryl, with a compound of formula (VIII)

$R_8$—X (VIII)

wherein $R_8$ is $C_1$-$C_6$ alkyl and X is a halogen atom, so obtaining a corresponding compound of formula (I), wherein W is a group

wherein one of $R_2$ and $R_3$ is $C_1$-$C_6$ alkyl and the other is $C_1$-$C_6$ alkyl, $C_5$-$C_6$ cycloalkyl, $C_6$-$C_9$ cycloalkylalkyl or aryl; or 5) dehydrogenating a compound of formula (I), wherein the symbol ═ is a single bond and $R_1$, Y, A and W are as defined above so obtaining a corresponding compound of formula (I), wherein the symbol ═ is a double bond; or 6) converting a compound corresponding to one of formula (I), wherein the symbol ═ is a single or double bond, A, Y and W are as defined above and $R_1$ is a protective group P of the amino function, into a corresponding compound of formula (I), wherein the symbol ═, A, Y and W are as defined above and $R_1$ is hydrogen; or 7) alkylating a compound of formula (I) wherein the symbol ═, W, Y and $R_1$ are as defined above, provided that $R_1$ does not represent hydrogen, and A is hydrogen, with a compound of formula (VIII), so obtaining a corresponding compound of formula (I) wherein A is a $C_1$-$C_6$ alkyl;

and if desired, converting a compound of formula (I) into a pharmaceutically acceptable salt thereof and/or, if desired, separating a mixture of isomers of formula (I) into the single isomers.

The reaction between a compound of formula (II) and a compound of formula (III) may be carried out, e.g., refluxing the compound of formula (II) with a large excess of the compound of formula (III) in an organic solvent, such as, for instance dioxane, toluene or xylene, or in pyridine in the presence of sodium, for a time from, e.g., about 1 hour to, e.g., about 48 hours under inert atmosphere, e.g of nitrogen.

In particular, for example, the reaction may be carried out by methods analogous to those described in Eur.J.Med.Chem. 24, 421-26 (1989); Chem Rev. 43, 203-18 (1948); or Chem Rev. 57, 49-51 (1957) or Chem. Rev. 53, 146 (1953).

The reaction between a compound of formula (IV) and a compound of formula (V) may be carried out, e.g., stirring the mixture of the two compounds in a suitable anhydrous solvent such as, for example, diethyl ether, benzene, dioxane, methylene chloride ($CH_2Cl_2$), dimethylformamide (DMF), tetrahydrofuran (THF) or their mixtures, optionally in the presence of an organic base, such as, for instance, pyridine or triethylamine (TEA).

The reaction temperature may range approximately from about 0° C. to the reflux temperature of the solvent; for instance, the reaction may be performed at room temperature for a time varying from about 2 hours to about 48 hours or following procedures similar to those described in, e.g., Chem.Rev. 53, 154–157 (1953); Chem. Rev. 67, 123–127 (1967); JOC 30 2849–51 (1965); or Eur.J.Med.Chem. 24, 421–26 (1989).

Alternatively the reaction may be carried out by gradual addition of a compound of formula (IV) to a compound of formula (V) in hot pyridine, as described in Chem.Ber. 72, 1735 (1939). The activating group X in the compounds of formula (VI) may be any suitable activating group of the carboxy function which is useful in the formation of amidic and peptidic linkages. It may be, for instance, one of the following groups:

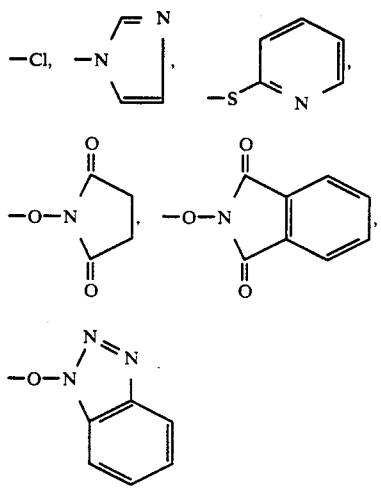

The reaction of a compound of formula (VI) with a compound of formula (VII) may be carried out in an anhydrous solvent such as, for instance, methylene chloride, dimethylformamide, tetrahydrofuran, benzene, toluene, or their mixtures, in the presence of an organic base such as, for example, pyridine, triethylamine, optionally in the presence of a catalytic amount of dimethylaminopyridine (DMAP) at a temperature ranging from about 0° C. to the reflux temperature of the solvent, preferably at room temperature, for a time varying from, e.g., about half an hour to, e.g., about 78 hours.

In the compound of formula (VIII) the halogen X may be, e.g., chlorine, bromine or iodine; in particular the compound $R_8$—X may be methyliodide.

The alkylation of a compound of formula (I) with a compound of formula (VIII) may be carried out in an inert atmosphere of, e.g., nitrogen, in the presence of an anhydrous solvent such as for instance DMF or THF, and of a stoichiometric amount of a strong base such as, e.g., butyl lithium or sodium hydride; the reaction temperature may range from about 0° C. to the reflux temperature of the solvent and the reaction times may vary approximately from about 1 hour to about 2 hours.

The dehydrogenation of a compound of formula (I) according to the above process variant 5), which is preferably performed on a compound of formula (I) wherein $R_1$ is hydrogen, may be carried out by treatment with a suitable dehydrogenating agent such as, e.g., chloranil, benzeneseleninic anhydride or dichlorodicyanobenzoquinone (DDQ), operating in an anhydrous solvent, such as, for example, chlorobenzene, dioxane, xylene, toluene or benzene, and, optionally, in the presence of BTSFA [bis(trimethylsilyl)trifluoro acetamide]. The reaction temperature may range from the room temperature to the reflux temperature of the solvent and the reaction time may vary approximately from about 2 hours to about 24 hours. Preferably the reaction is carried out under inert atmosphere, e.g., nitrogen atmosphere.

The protective group P of the amino function, indicated above under 6) may be, e.g., an optionally substituted aryl $C_1$–$C_6$ group, preferably benzyl or p-methoxybenzyl, an aroyl group preferably, benzoyl; or an alkylsilyl group preferably tert-butyl dimethylsilyl.

The conversion indicated above as process variant 6) may be carried out following known methods. For instance, when P is a protecting group such as benzyl or benzoyl its removal to give a corresponding compound of formula (I) wherein $R_1$ is hydrogen, may be carried out by hydrogenation under a pressure of, e.g., from 1 to 5 atmosphere of hydrogen, in the presence of a catalyst such as, e.g., Pd/C, Raney-Nichel, and operating in a suitable solvent such as, e.g., dioxane, ethyl acetate, acetic acid, 1N hydrocloric acid or a mixture of said solvents, at a temperature ranging, e.g., from about the room temperature to about 80° C., for a time varying from about 2 hours to about 24 hours.

When P is an alkylsilyl protective group such as, e.g., tert-butyldimethylsilyl, its removal may be carried out, for example, by treatment with tetrabutyl ammonium fluoride or with aqueous hydrofluoric acid in a solvent such as, for example, tetrahydrofuran or acetonitrile, at a temperature ranging from about 0° C. to about 50° C., for a time varing from about 10 minutes to 24 hours.

The alkylation of a compound of formula (I) with a compound of formula (VIII) according to the above process variant 7 may be carried out in an inert atmosphere of, e.g., nitrogen in the presence of an anhydrous solvent such as for instance DMF or THF, and of a stoichiometric amount of an inorganic base such as, e.g., potassium hydroxide or sodium hydroxide; the reaction temperature may range from about 0° C. to the reflux temperature of the solvent and the reaction times may vary approximately from about 1 hours to about 4 hours. Standard procedures may be used for converting a compound of formula (I) into a pharmaceutically acceptable salt thereof as well as for separating a mixture of isomers of formula (I) into the single isomers.

The compounds of formula (III), (V), (VII) and (VIII) are commercially available products or they can be prepared by known methods described in the literature.

A compound of formula (II) may be obtained reacting a compound of formula (VI), wherein the symbol , X and $R_1$ are as defined above, with a compound of formula (IX)

 A—NH$_2$ (IX)

wherein A has the meanings above defined.

The reaction may be carried out operating, e.g., in an inert solvent such as, for example, CH$_2$Cl$_2$, THF, AcOEt, (ethylacetate) DMF, benzene, toluene at a temperature ranging from about 0° C. to about 100° C., and, optionally, in the presence of a base such as, for example, pyridine, p-dimethylaminopyridine or a tri-$C_1$-$C_6$ alkylamine, for a time variyng from about 1 hour to about 24 hours.

The compound of formula (IX) is a commercially available product or can be prepared according to known methods.

A compound of formula (VI) may be obtained from a compound of formula (IV) wherein Y is oxygen according to known procedures.

In particular a compound of formula (VI) wherein X is a group —Cl may be obtained according to the method described in JACS 70, 2427 (1948); Helv.Chim. Acta 37, 45 (1954); Can. J. Chem. 33, 1515 (1955).

A compound of formula (VI), wherein X is a group

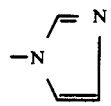

may be obtained according to the method described in Angew. Chem. 74, 407 (1962);

A compound of formula (VI) wherein X is a group

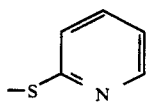

may be obtained according to the method described in Tetr. 33, 683 (1977);

A compound of formula (VI) wherein X is a group

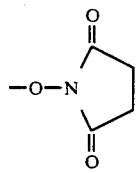

may be obtained according to the method described in JACS 86, 1839, (1964); or Z-Naturforsch B 21, 426, (1966).

A compound of formula (VI) wherein X is a group

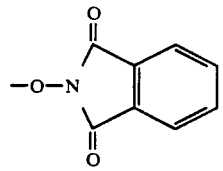

may be obtained according to the method described in JACS 83, 1263 (1961).

A compound of formula (VI) wherein X is a group

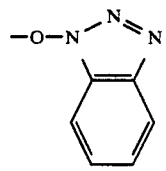

may be obtained according to the method described in Chem. Ber. 103, 788 (1970).

The compounds of formula IV wherein Y is sulfur, which are novel compounds, may be, e.g., obtained from compounds of formula (VI) according to known procedures.

One procedure may involve, for example, reacting a compound of formula (VI) wherein X is chlorine, with gaseous hydrogen sulfide in the presence of dimethyl-thioformamide, in a solvent such as, for example, $CH_2Cl_2$, at room temperature for a time varying from, e.g., ten minutes to some hours under vigorous stirring, according to the method described in Synthesis, 671-2 (1985).

Another procedure may involve, e.g., reacting a compound of formula (VI) wherein X is

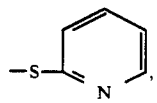

that it is the S-2-pyridylthioate derivative, with an excess of sodium hydrogen sulfide monohydrate. The reaction may be performed in a solvent such as, for example, methylene chloride, tetrahydrofurane, acetonitrile, at a temperature ranging from, e.g., about 0° C. to about 50° C., for a time varying, e.g., from about one hour to about 48 hours.

A compound of formula (IV) wherein Y is sulphur may also be synthesized according to the general methods described in the literature for the synthesis of thiocarboxylic acids, for example in analogous way as described in Houben Weyl, Bd E 5, pages 832-842 or by Duns F. in Barton and Ollis. Comprehensive Organic chemistry, Vol. 3 Pergamon Press, Oxford, 1979, pages 420-32.

The compounds of formula (IV) wherein Y is oxygen are known compounds [see, for example, J. Med.Chem. 27, 1690-1701 (1984) and J. Med.Chem. 29, 2298-315, 1986)] or may be prepared following procedures known in the organic chemistry.

For example, a compound of formula (IV) wherein Y is oxygen and the symbol ≡ is a double bond may be obtained dehydrogenating a corresponding compound of formula (IV), where the symbol ≡ is a single bond.

This dehydrogenation may be performed with a dehydrogenating agent, such as, e.g., benzeneseleninic anhydride or DDQ, in a suitable anhydrous solvent such as, for example, chlorobenzene, toluene, xylene, dioxane, optionally operating in the presence of BTSFA, at a temperature ranging e.g., from the room temperature to the reflux temperature of the solvent, for a time varying approximately from about two hours to about 24 hours, preferably under an inert atmosphere of, e.g., nitrogen.

The compound of formula (IV) wherein Y is oxygen and the symbol ≡ is a single bond may in its turn be obtained according to the procedure illustrated in the following reaction scheme:

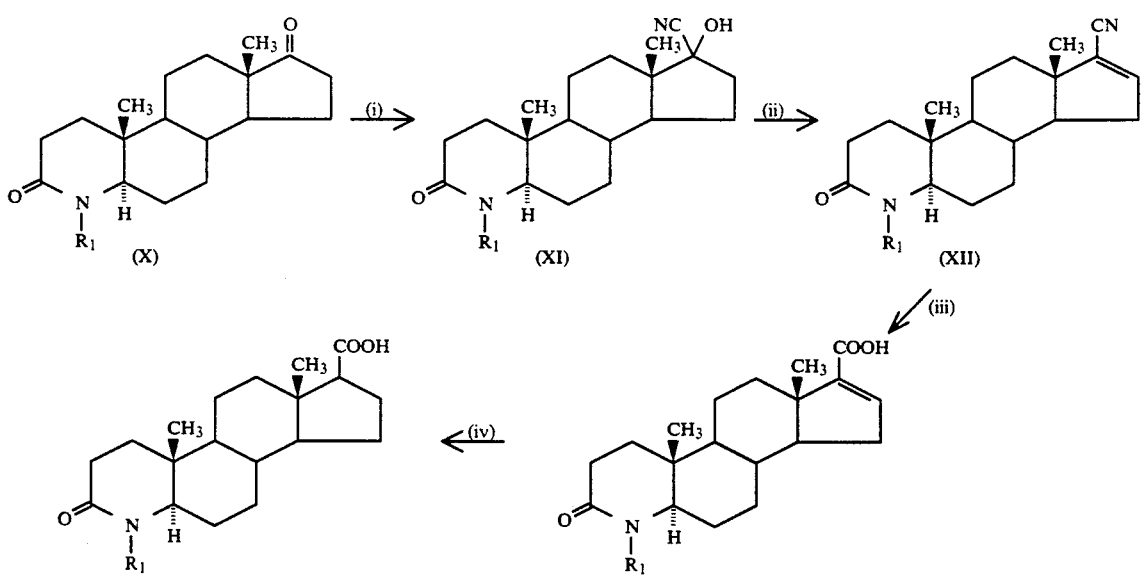

The compound of formula (X) is a known compound: see, for example, J.O.C. 46, 1442–46 (1981).

According to reaction step (i) the cyanohydrins of formula (XI) may be obtained from the ketones of formula (X), by reacting the latter with, e.g., potassium cyanide in acetic acid or with the acetone cyanohydrin, at a temperature ranging, e.g., from about 10° C. to about 50° C. for a time varying from about half an hour to about 3 hours.

The dehydration of a compound of formula (XI) to give a compound of formula (XII) according to reaction step (ii) may be carried out with a dehydrating agent such as, for example, phosphorus oxychloride or thionyl chloride, operating in a inert solvent, such as, e.g., pyridine either alone or admixed with another inert solvent, such as, e.g., benzene, toluene or methylene chloride, operating at a temperature ranging from the room temperature to the boiling temperature of the solvent, for a time which may vary, e.g., from about some minutes to about some hours.

The hydrolysis of a compound of formula (XII) to give a compound of formula (XIII) according to reaction step (iii) may be, e.g., carried out with a concentrated alkali metal hydroxide solution such as, e.g., 35% acqueous sodium hydroxide, optionally operating in the presence of a cosolvent such as, e.g., methanol, ethanol ethylenglycol, tetrahydrofurane or dioxane either at atmospheric pressure or in a sealed vessel, at a temperature ranging, e.g., from the room temperature to around 200° C., for a time varying approximately from some hours to 24 hours.

The hydrogenation of a compound of formula (XIII) to give a compound of formula (IV) according to reaction step (iv) may be carried out, e.g., in an alkali metal hydroxide solution, such as for instance 2N sodium hydroxide, optionally in the presence of a cosolvent, e.g., ethyl alcohol, and using an hydrogenation catalyst, such as, e.g., Raney-Nickel, and preferably using hydrogen at atmospheric pressure.

The compounds of the present invention inhibit specifically the testosterone 5α-reductase enzyme and, therefore, can be useful for the treatment of androgen-dependent conditions. For example, the inhibitory effect of the compounds of the invention on 5α-reductase was determined in vitro in comparison with progesterone taken as the reference compound, according to the procedure reported herebelow.

Inhibition of 5α-reductase was evaluated using the particulate fraction (containing nuclei, microsomes and mitochondria) from homogenates of human benign prostatic hypertrophy tissue as the enzyme source. The particulate fraction was prepared centrifuging prostate homogenate at 40,000×g. The resulting pellet, washed several times, was resuspended in buffer and stored at $-80°$ C. in aliquots containing $\approx 10$ mg protein/ml.

The assay for 5α-reductase was done in a final volume of 0.5 ml, containing 1 mM dithiothreitol, 40 mM TRIS-HCl buffer pH 5.0, 5 mM NADPH, 1 μM [4-$^{14}$C]testosterone, 0.3 mg of prostate particulate fraction and various concentrations of the inhibitors. After 30 min incubation at 37° C. the reaction was terminated by addition of 1.5 ml diethyl ether and the organic phase was separated, evaporated under N$_2$ and resuspended in ethyl acetate. Testosterone metabolites in this extract were separated in TLC on silica gel F 254 plates (Merck) using chloroform, acetone and n-hexane (2:1:2) as developing solvent system. Radioactivity on the plate was scanned and analyzed from quantitative plots printed by a TLC-analyzer (Berthold). The fractional 5α-reduction of testosterone was calculated by relating the $^{14}$C-radioactivity in the 5α-reduced metabolites (5α-dihydrotestosterone, 3α- and 3β-androstanediols) regions to the total radioactivity in the testosterone and 5α-reduced metabolites regions.

The concentration of each compound required to reduce control 5α-reductase by 50% (IC$_{50}$) was determined by plotting % inhibition versus log of inhibitor concentration.

As an example, the potency of three representative compounds of the invention, namely 4-methyl-17β-[N-isopropyl-N-(N-isopropylcarbamoyl)carbamoyl]-4-aza-5α-androstan-3-one (Compound 1), 4-methyl-17β-[N-cyclohexyl-N-(N-cyclohexylcarbamoyl) carbamoyl-4-aza-5α-androstan-3-one (Compound 11) and 4-methyl-17β-[N-isopropyl-N-(N-isopropylthiocarbamoyl)carbamoyl-4-aza-5α-androstan-3-one (Compound 39) are reported in Table 1 in comparison with progesterone.

TABLE 1

| Inhibition of prostatic 5α-reductase | |
|---|---|
| Compound | IC$_{50}$ nM |
| Progesterone | 1980 |
| Compound 1 | 55 |
| Compound 11 | 41 |
| Compound 39 | 11 |

The compounds of the invention were also tested for their in vivo potency in inhibiting 5α-reductase of rat prostate, according to the following procedure.

Prepuberal 21-day old male rat were castrated via scrotal incision in light ether anaesthesia.

Starting on the seventh day after orchiectomy, the rats were treated with testosterone propionate (0.3 mg/kg/day subcutaneously) for 7 consecutive days to stimulate prostate growth. The 5α-reductase inhibitors were given orally at various doses once daily for 7 days, together with the standard dose of testosterone propionate.

Thus, for example, in the above test the compound 1 of the present invention was compared with the well known 5α-reductase inhibitor 4-methyl-17β-N,N-diethyl-carbamoyl-4-methyl-4-aza-5α-androstan-3-one, identified as 4-MA and described, e.g., in U.S. Pat. No. 4,377,584) giving the results reported in the following Table 2.

TABLE 2

| Inhibition of prostate growth stimulated by testosterone propionate in castrated rats | | |
|---|---|---|
| Compound | Dose mg/kg/day p.o. | Inhibition % |
| 4-MA | 3 | 1 |
|  | 10 | 0 |
|  | 30 | 49 |
| Compound 1 | 3 | 33 |
|  | 10 | 55 |

The data on Table 2 show that the compound of the present invention is a very effective 5α-reductase inhibitor in vivo in that causing, at the oral dose of 10 mg/kg/day, a decrease of the hypertrophic response to testosterone propionate by 55%. In contrast, at the same dose, 4-MA was completely ineffective.

For their use in androgen- dependent conditions, the 5α-reductase inhibitors, should have a very low intrinsic androgenic activity, which can be shown by the binding affinity to the androgen receptor.

A low binding affinity to the androgen receptor is therefore desirable in a 5α-reductase inhibitor for use in the treatment of androgen dependent conditions.

Binding affinity to cytoplasmic androgen (rat prostate) receptors was determined by standard dextran-coated absorption technique (Raynaud J. P. et al., J. Steroid. Biochem. 6: 615–622, 1975).

Prostatic tissue, obtained from adrenalectomized and castrated Sprague-Dawley rats, was homogenized in 10 mM Tris HCl pH 7.4, containing 1.5 mM EDTA and 1 mM dithiothreitol in motor driven tissue grinders. The homogenate was centrifuged at 10,000×g for 1 h at 4° C.

Aliquots of cytosol 00.2 ml) were incubated for 2 hours at 0° C. with various concentrations of the test compounds, in duplicate, and a fixed amount of $^3$H-dihydrotesterone (DHT) final concentration 1 nM in 0.4 ml of incubation volume).

Then, free radioactivity was absorbed on 0.2 ml of dextran-coated charcoal suspension and after centrifugation at 1,500×g for 10 min., the bound radioactivity in the supernatant was determined by liquid scintillation in Rialuma.

The concentration of each compound required to reduce specific $^3$H-DHT binding by 50% (IC$_{50}$) was determined from a plot of bound radioactivity versus log of competitor concentration.

In the above test the Compound 1 of the present invention was compared with the same above identified reference compound 4-MA and the obtained results are reported in the following Table 3.

TABLE 3

| Rat prostate androgen receptor binding | |
|---|---|
| Compound | Inhibition of DHT binding IC$_{50}$ (nM) |
| 4-MA | 2,500 |
| Compound 1 | 150,000 |

As shown in Table 3, Compound 1 displaces DHT from the prostatic androgen receptor only at a very high concentration, thus resulting more selective than the reference compound 4-MA, which, in contrast, displaces DHT at a concentration 60 times lower.

The above results show that the compounds of the present invention are very potent and selective 5α-reductase inhibitors.

In view of the before indicated activity the compounds of the invention are therapeutically useful in the situations in which a decrease in androgen action, by means of 5α-reductase inhibition, is desirable such as, for example, benign prostatic hyperplasia, prostatic and breast cancers and certain skin-hair conditions such as, e.g., acne, seborrhoea, female hirsutism and male pattern baldness.

They are useful both in the pharmaceutical field and, e.g., for the treatment of prostatic hyperplasia, in the veterinary field.

The toxicity of the compounds of the invention is quite negligible so that they can be safely used in therapy.

The compounds of the invention can be administered in a variety of dosage forms, e.g. orally, in the form of tablets, capsules, sugar or film coated tablets, liquid solutions or suspensions; rectally, in the form of suppositories; parenterally, e.g., intramuscularly, or by intravenous injection or infusion; topically, e.g., in the form of creams.

The dosage depends on the age, weight, conditions of the patient and administration route; for example the dosage adopted for oral administration to adult humans may range from about 1 to about 200 mg pro dose, from 1 to 3 times daily.

As already said the invention includes pharmaceutical compositions comprising a compound of the invention in association with a pharmaceutically acceptable excipient (which can be a carrier or diluent).

The pharmaceutical compositions containing the compounds of the invention are usually prepared following conventional methods and are administered in a pharmaceutically suitable form.

For example, the solid oral forms may contain, together with the active compound, diluents, e.g., lactose, dextrose, saccharose, cellulose, corn starch or potato starch; lubricants, e.g. silica, talc, stearic acid, magnesium or calcium stearate, and/or polyethylene glycols; binding agents, e.g. starches, arabic gums, gelatin, methylcellulose, carboxymethylcellulose or polyvinyl pyrrolidone; disaggregating agents, e.g. a starch, alginic acid, alginates or sodium starch glycolate; effervescing mixtures; dyestuffs; sweeteners; wetting agents, such as lecithin, polysorbates, laurylsulphates; and, in general, non-toxic and pharmacologically inactive substances used in pharmaceutical formulations. Said pharmaceutical preparations may be manufactured in known manner, for example, by means of mixing granulating, tabletting, sugar-coating, or film-coating processes.

The liquid dispersions for oral administration may be e.g., syrups, emulsions and suspensions.

The syrups may contain as carrier, for example, saccharose or saccharose with glycerine and/or mannitol and/or sorbitol; in particular a syrup to be administered to diabetic patients can contain as carriers only products not metabolizable to glucose, or metabolizable in very small amount to glucose, for example sorbitol.

The suspensions and the emulsions may contain as carrier, for example, a natural gum, agar, sodium alginate, pectin, methylcellulose, carboxymethylcellulose, or polyvinyl alcohol.

The suspensions or solutions for intramuscular injections may contain, together with the active compound, a pharmaceutically acceptable carrier, e.g. sterile water, olive oil, ethyl oleate, glycol, e.g. propylene glycol and if desired, a suitable amount of lidocaine hydrochloride.

The solutions for intravenous injections or infusions may contain as carrier, for example, sterile water or preferably they may be in the form of sterile, aqueous, isotonic saline solutions.

The suppositories may contain together with the active compound a pharmaceutically acceptable carrier, e.g. cocoa-butter, polyethylene glycol, a polyoxyethylene sorbitan fatty acid ester surfactant or lecithin. Conventional carriers may be used for topical formulations. The terms "pharmaceutical" and the like as used in the present specification are meant to include also the meanings "veterinary and the like.

The following examples illustrate but do not limit the invention.

The reported NMR data (δ ppm) are determined in CDCl$_3$.

EXAMPLE 1

4-methyl-17$\beta$-{N-[3-(dimethylamino)propyl]carbamoyl}-4-aza-5$\alpha$-androstan-3-one.

A mixture of S-2-pyridyl-4-methyl-4-aza-5$\alpha$-androstan-17$\beta$-carboxylate (500 mg) in methylene chloride (25 ml) and 3-dimethylaminopropylamine (1.06 ml) is stirred at room temperature overnight.

The solvent is removed under vacuum and the crude is chromatographed on silica gel, eluting with chloroform methanol (80/15), so obtaining 300 mg of the title compound as a white solid, m.p. 224°-226° C.;

Elemental analysis:
Calculated for C$_{25}$H$_{43}$N$_3$O$_2$: C 71.90; H 10.38; N 10.06; found C 72.60; H 10.48; N 10.18;
IR (nujol): 3180, 1674, 1638 cm$^{-1}$;
NMR (CDCl$_3$): 6.95 (t, 1H, CONHCH$_2$), 3.0–3.6 (m, 3H, CONHCH, CONHCH$_2$), 2.89 (t, 2H, CH$_2$N<), 2.66

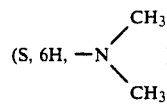

0.9 (s, 3H, CH$_3$(19)), 0.69 (s,3H, CH$_3$(18));
MS (m/z): 417 M+·, 58 CH$_2$=N+(CH$_3$)$_2$

Following analogous procedure, the below listed compounds can be prepared:
4-methyl-17$\beta$-(N-neopentylcarbamoyl)-4-aza-5$\alpha$-androstan-3-one, m.p. 187°-189° C.;
4-methyl-17$\beta$-(N-neopentylcarbamoyl)-4-aza-5$\alpha$-androst-1-en-3-one, m.p. 143°-145° C.;
4-methyl-17$\beta$-[N-(3-ethoxypropyl)carbamoyl]-4-aza-5$\alpha$-androstan-3-one, m.p. 110°-112° C.;
4-methyl-17$\beta$-[N-(3-ethoxypropyl)carbamoyl]-4-aza-5$\alpha$-androst-1-en-3-one, m.p. 92°-95° C.; and
4-methyl-17$\beta$-{-[3-(dimethylamino)propyl]carbamoyl}-4-aza-5$\alpha$-androst-1-en-3-one, m.p. 182°-185° C.

EXAMPLE 2

4-methyl-17$\beta$-{N-[3-(dimethylamino)propyl]-N-(N-ethylcarbamoyl)carbamoyl}-4-aza-5$\alpha$-androstan-3-one hydrochloride A mixture of 17$\beta$-{N-[3-(dimethylamino)propyl]carbamoyl}-4-aza-5$\alpha$-androstan-3-one (300 mg) in anhydrous toluene (6 ml) and ethylisocyanate (1.16 ml) is refluxed for 24 hours. The reaction mixture is evaporated to give an oil which is dissolved in chloroform, washed several times with brine and dried over sodium sulphate.

The solvent is removed under vacuum and the crude compound is chromatographed on silica gel eluting with methylene chloride/methanol (90/10).

After evaporation of the eluant, the oil is dissolved in methylene chloride, treated with gaseous hydrochloric acid, and crystallized from methylene chloride/diethyl ether to afford 105 mg of the title compound as a white solid, m.p. 115°-120° C.;

Elemental analysis: Calculated for C$_{28}$H$_{48}$N$_4$O$_3$.HCl, C 64.04, H 9.40, N 10.67, Cl 6.75, found, C 63.32, H 9.51, N 10.74,Cl 6.83,
IR (nujol): 3170, 1690, 1650, 1630 cm$^{-1}$;
NMR (CDCl$_3$): 9.28

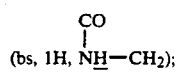

3.82 (m, 2H, CO—N—CH$_2$) 3.28 (dg, 1H, —NH—CH-2—CH$_3$), 3.05 (dd, 1H, $\overline{\text{H}}$ (5$\alpha$)), 2.91 (s, 3H, N—C$\overline{\text{H}_3}$), 2.55

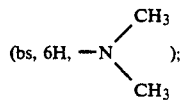

1.17 (t. 3H, NH—CH$_2$CH$_3$), 0.87 (s, 3H, CH$_3$(19)); 0.73 (s, 3H, CH$_3$(18));
MS (m/z): 488 M+·; 417 M+·—OCN—C$_2$H$_5$; 58 CH$_2$=N+(CH$_3$)$_2$

Following analogous procedure, the below listed compounds can be prepared:

4-methyl-17β-{N-[3-(dimethylamino)propyl]-N-(N-ethyl carbamoyl)carbamoyl}-4-aza-5α-androst-1-en-3-one hydrochloride, m.p. 160°–164° C.;

4-methyl-17β-[N-neopentyl-N-(N-ethylcarbamoyl)carbamoyl]aza-5α-androstan-3-one, m.p. 166°–169° C.;

4-methyl-17β-[N-neopentyl-N-(N-ethylcarbamoyl)carbamoyl]-4-aza-5α-androst-1-en-3-one, m.p. 129°–131° C.;

4-methyl-17β-[N-(3-ethoxy-1-propyl)-N-(N-ethylcarbamoyl) carbamoyl]-4-aza-5α-androstan-3-one, m.p. 98°–103° C.;

4-methyl-17β-[N-(3-ethoxy-1-propyl)-N-(N-ethylcarbamoyl) carbamoyl]-4-aza-5α-androst-1-en-3-one, m.p. 78°–82° C.;

4-methyl-17β-[N-isopropyl-N-(N-phenylcarbamoyl)carbamoyl-4-aza-5α-androst-1-en-3-one, m.p. 210°–212° C.;

4-methyl-17β-[N-(N-tert-butylcarbamoyl)carbamoyl]-4-aza-5α-androstan-3-one. m.p. 220°–225° C.;

4-methyl-17β-[N-(N-tert-butylcarbamoyl)carbamoyl]-4-aza-5α-androst-1-en-3-one, m.p. 250°–254° C.;

4-methyl-17β-[N-(N-butylcarbamoyl)carbamoyl]-4-aza-5α-androstan-3-one, m.p. 142°–146° C.; and 4-methyl-17β-[N-(N-butylcarbamoyl)carbamoyl]-4-aza-5α-androst-1-en-3-one, m.p. 160°–163° C.

Using the appropriate isothiocyanate, instead of isocyanate, and following analogous procedure, the below listed compounds can be prepared:

4-methyl-17β-{N-[3-(dimethylamino)propyl]-N-N-ethylthiocarbamoyl)carbamoyl}-4-aza-5α-androstan-3-one hydrochloride, m.p. 103°–108° C.;

4-methyl-17β-{N-[3-[dimethylamino)propyl]-N-(N-ethylthio carbamoyl)carbamoyl}-4-aza-5α-androst-1-en-3-one hydrochloride, m.p. 134°–136° C.;

4-methyl-17β-[N-neopentyl-N-(N-ethylthiocarbamoyl)carbamoyl]-4-aza-5α-androstan-3-one;

4-methyl-17β-[N-neopentyl-N-(N-ethylthiocarbamoyl)carbamoyl]-4-aza-5α-androst-1-en-3-one;

4-methyl-17β-[N-(3-ethoxy-1-propyl)-N-(N-ethylthiocarbamoyl) carbamoyl]-4-aza-5α-androstan-3-one;

4-methyl-17β-[N-(3-ethoxy-1-propyl)-N-(N-ethylthiocarbamoyl) carbamoyl]-4-aza-5α-androst-1-en-3-one;

4-methyl-17β-[N-isopropyl-N-(N-phenylthiocarbamoyl)carbamoyl-4-aza-5α-androst-1-en-3-one, m.p. 211°–215° C.;

4-methyl-17β-[N-(N-tert-butylthiocarbamoyl)carbamoyl]-4-aza-5α-androstan-3-one. m.p. 183°–185° C. dec.;

4-methyl-17β-[N-(N-tert-butylthiocarbamoyl)carbamoyl]-4-aza-5α-androst-1-en-3-one, m.p. 192°–194° C. dec.;

4-methyl-17β-[N-(N-butylthiocarbamoyl)carbamoyl]-4-aza-5α-androstan-3-one, m.p. 102°–103° C.; and 4-methyl-17β-[N-(N-butylthiocarbamoyl)carbamoyl]-4-aza-5α-androst-1-en-3-one, m.p. 108°–111° C.

EXAMPLE 3

4-methyl-17β-{N-isopropyl-N-(N-isopropylcarbamoyl)carbamoyl}-4-aza-5α-androstan-3-one A suspension of 4-methyl-4-aza-5α-androstan-3-one-17β-carboxylic acid (410 mg) in methylene chloride (55 ml) is treated with N,N'-diisopropylcarbodiimide (0.207 ml) and stirred overnight at room temperature.

The solvent is removed under vacuum, and the solid is dissolved in ethylacetate/benzene (1/1) (100 ml), washed with 0.1N aqueous sodium bicarbonate, 1N hydrochloric acid, brine and dried over sodium sulphate.

Evaporation of the solvent leaves 540 mg of solid, that is purified by flash chromatography on $SiO_2$, eluting with methylene chloride/acetone (70/30), to obtain 310 mg of the title compound as white solid, m.p. 175°–176° C., Elemental analysis:

Calculated for $C_{27}H_{45}N_3O_3$: C 70.55; H 9.87; N 9.14: found: C 70.30; H 9.97; N 8.90;

IR (nujol): 3170, 1690, 1652, 1632, 15440 $cm^{-1}$;

NMR(CDCl$_3$): 6.42 (bm, 1H, CONH), 4.47

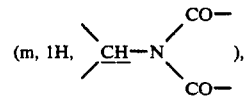

(m, 1H, CH—N(CO—)(CO—)), 3.97 (m, 1H, —CONH—CH<); 2.99 (dd, 1H, H(5α), 2.97 (s, 3H, N—CH$_3$), 2.69 (t, 1H, —H(17β)), 1.20–1.33 (4d, 12H, 4 isopropylic CH$_3$), 0.875 (s. 3H, CH$_3$(19)), 0.77 (s, 3H, CH$_3$(18));

MS(m/z) 459 $M^+$·, 374 M - OCN—CH(CH$_3$)$_2$$^+$·, 85 OCN—CH(CH$_3$)$_2$$^+$·

Following analogous procedure, the below listed compounds can be prepared:

4-methyl-17β-[N-tert-butyl-N-(N-tert-butylcarbamoyl)-carbamoyl]-4-aza-5α-androstan-3-one, m.p. 166°–168° C. dec.;

4-methyl-17β-[N-cyclohexyl-N-(N-cyclohexylcarbamoyl)carbamoyl]-4-aza-5α-androstan-3-one, m.p. 182°–183° C.;

4-methyl-17β-{N-[3-(dimethylamino)propyl]-N-(N-ethylcarbamoyl)carbamoyl}-4-aza-5α-androstan-3-one hydrochloride, m.p. 116°–120° C.; and 4-methyl-17β-[N-cyclohexylmethyl-N-(N-cyclohexylmethylcarbamoyl)carbamoyl]-4-aza-5α-androstan-3-one, m.p. 167°–171° C.

EXAMPLE 4

4-methyl-17β-[N-isopropyl-N-(N-isopropylcarbamoyl)-carbamoyl]-4-aza-5α-androst-1-en-3-one A suspension of 4-methyl-4-aza-5α-androst-1-en-3-one 17β-carboxylic acid (440mg) in methylene chloride (22 ml) is treated with N,N'-diisopropylcarbodiimide (0.226 ml) and stirred at room temperature for 2 hours.

The solvent is removed under vacuum and the solid is dissolved in ethylacetate (40 ml); the organic solution is then washed with 0.1 M sodium bicarbonate, 1N hydrochloric acid, brine and dried over sodium sulphate.

The crude solid, obtained after evaporation of the solvent, is purified by chromatography on $SiO_2$ (eluant chloroform/acetone 70/30), thus obtaining 300 mg of a solid compound, that is crystallized twice (from acetone/methylene chloride and from acetone) to afford 240 mg of the title compound as a white crystalline product, m.p. 208°–210° C.;

Elemental analysis:

Calculated for $C_{27}H_{43}N_3O_3$: C 70.86; H 9.47; N 9.18; found: C 70.78; H 9.40; N 9.18;

IR (nujol): 3180, 1688, 1652, 1593, 1540 $cm^{-1}$;

NMR (CDCl$_3$) : 6.69 (d, 1H, H(1)), 6.38 (m, 1H, CONH); 5.86 (dd, 1H, H(2)), 4.50

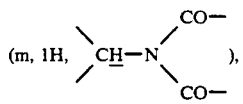

4.00 (m, 1H, —CONH—CH<), 3.35 (dd, 1H, H(5α)), 2.97 (s, 3H, N—CH₃), 2.72 (t, 1H, —H(17α), 1.36–1.15 (4d, 12H, 4 isopropylic CH₃), 0.94 (s, 3H, CH₃(19)), 0.81 (s, 3H, CH₃(18)).

Following analogous procedure the below listed compounds can be prepared:

4-methyl-17β-[N-tert-butyl-N-(N-tert-butylcarbamoyl) carbamoyl]-4-aza-5α-androst-1-en-3-one, m.p. 196°–199° C.;

4-methyl-17β-[N-cyclohexyl-N-(N-cyclohexylcarbamoyl) carbamoyl]-4-aza-5α-androst-1-en-3-one, m.p. 213°–215° C.; and 4-methyl-17β-{N-[3-(dimethylamino)propyl]-N-(N-ethylcarbamoyl)carbamoyl}-4-aza-5α-androst-1-en-3-one hydrochloride, m.p 160°–164° C.

EXAMPLE 5

17β-[N-isopropyl-N-(N-isopropylcarbamoyl)carbamoyl]-4-aza-5α-androstan-3-one

To a solution of diisopropylcarbodiimide (60 mg) in anhydrous pyridine (6.5 ml), 4-aza-5α-androstan-3-one-17β-carboxylic acid (100 mg) is added and the mixture is stirred at 85° C. for 8 hours under nitrogen atmosphere, a further amount of diisopropylcarbodiimide (20 mg) is added and the stirring is continued for 8 hours at 85° C. under nitrogen atmosphere.

The reaction mixture is poured into 1N hydrochloric acid (100 ml) and extracted with methylene chloride (3×20 ml); the organic extracts are washed with brine, until they are neutral, dried over sodium sulphate and the solvent removed under vacuum.

The crude (153 mg) is chromatographed on silica gel, eluting with methylene chloride/acetone (55:45), so obtaining 86 mg of the title compound, m.p. 210°–212° C.;

Elemental analysis:
Calculated for C₂₆H₄₃N₃O₃, C 70.07, H 9.73, N 9.43, found: C 70.14, H 9.84, N 9.34, IR (nujol): 3260, 3170, 1690, 1660–1630, 1548 cm⁻¹

NMR (CHCl₃): 6.55 (m, 1H, >NCONH), 6.26 (bs, 1H, NH(4)) 4.47

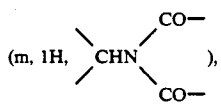

3.97 (m, 1H, —CONH—CH<), 3.08 (dd, 1H, H(5α)), 2.69 (t, 1H, —H(17α)), 1.22–1,34 (4d, 12H, 4-isopropylic.CH₃), 0.89 (s, 3H, CH₃(19)), 0.78 (s, 3H, C₃(18)).

(MS m/e): 445 M+.
360 M - OCN—CH(CH₃)₂⁷⁺·
345 360—.CH₃⁷⁺·
85 OCN—CH(CH₃)₂⁷⁺·
70 85 - —CH₃.₇+.

Following analogous procedure, the below listed compounds can be prepared:

17β-[N-tert-butyl-N-(N-tert-butylcarbamoyl)carbamoyl]-4-aza-5α-androstan-3-one, m.p. 198°–201° C.;

17β-[N-cyclohexyl-N-(N-cyclohexylcarbamoyl)carbamoyl]-4-aza-5α-androstan-3-one, m.p. 215°–217° C. and;

·17β{N-[3-(dimethylamino)propyl]-N-(N-ethylcarbamoyl) carbamoyl}-4-aza-5α-androstan-3-one hydrochloride, m.p. 150°–154° C.;

EXAMPLE 6

17β-[N-isopropyl-N-(N-isopropylcarbamoyl)carbamoyl]-4-aza-5α-androst-1-en-3-one

To a solution of diisopropylcarbodiimide (1.7 ml) in anhydrous pyridine (152 ml), mantained under inert atmosphere of nitrogen at room temperature, 4-aza-5α-androst-1-en-3-one 17β-carboxylic acid (2.39 g) is added in one portion.

The reaction mixture is heated at 80° C. for 6 hours then it is cooled with an ice-water bath and then water (500 ml) is added dropwise.

The mixture is kept at −20° C. for 60 hours; the precipitate which is formed is filtered by suction filtration, washed with water and dried under vacuum at 50° C. for 15 hours to give 2.08 g of the title product as a white solid, m.p. 285°–287° C.

Elemental analysis:
Calculated for C₂₆H₄₁N₃O₃: C 70.39, H 9.32, N 9.47, found: C 70.23, H 9.31, N 9.38, IR (nujol): 3260, 3170, 1688, 1663, 1645, 1600, 1548 cm⁻¹;

NMR(CDCl₃): 7.50 (d, 1H, H(1)), 6.38 (bm, 1H, —CONH—) 5.78 (dd, 1H,H(2)), 5.4 (m, 1H,NH(4)), 4.46

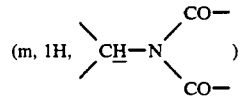

3.96 (m, 1H, —CONH—CH<), 3.29 (dd, 1H, H(5α)), 2.68 (t, 1H, H(17α)), 2.15 (m, 2H, CH₂(16)), 1.17–1.33 (4d, 12H, 4 isopropylic CH₃), 0.95 (s, 3H, CH₃(19)), 0.77 (s, 3H, CH₃(18)).

MS (m/e) 443 M+·, 358 M - ONC—CH(CH₃)₂⁷+·

Following analogous procedure, the below listed compounds can be prepared:

17β-[N-tert-butyl-N-(N-tert-butylcarbamoyl)carbamoyl]-4-aza-5α-androst-1en-3-one, m.p. 273°–276° C.;

17β-[N-cyclohexyl-N-(N-cyclohexylcarbamoyl)carbamoyl]-4-aza-5α-androst-1-en-3-one, m.p. 290°–292° C.;

17β-{N-[3-(dimethylamino)propyl]-N-(N-ethylcarbamoyl) carbamoyl}-4-aza-5α-androst-1-en-3-one hydrochloride, m.p. 220°–224° C.; and 17β-[N-cyclohexylmethyl-N-(N-cyclohexylmethylcarbamoyl) carbamoyl]-4-aza-5α-androst-1-en-3-one, m.p. 274°–277° C.

EXAMPLE 7

4-methyl-17β-[N-isopropyl-N-(N-isopropylthiocarbamoyl) carbamoyl]-4-aza-5α-androstan-3-one To a suspension of 4-methyl-4-aza-5α-androstan-3-one-17β-carboxylic acid (400 mg) in anhydrous toluene (52 ml), kept under nitrogen atmosphere, oxalyl chloride (0.955 ml) is added and the mixture is stirred at room temperature for 20 minutes.

The solvent is removed under vacuum and the yellow solid residue is dissolved in methylene chloride (2.4 ml);

dimethylthioformamide (0.125 ml) is added and gaseous hydrogen sulfide is passed into the mixture at moderate rate with vigorous stirring, for 20 min. at room temperature; the reaction mixture is then stirred at room temperature for further 40 minutes.

The CH$_2$Cl$_2$ is removed under reduced pressure at room temperature and the solid residue is taken up with Et$_2$O and filtered by suction filtration, washed with Et$_2$O and dried at 40° C. under vacuum (0.1 mmHg).

There are obtained 432 mg of crude thioacid as a violet solid, m.p. 240°–245° C.;

IR (nujol): 2600–2550, 1720, 1660 cm$^{-1}$.

The crude thioacid (432 mg) is dissolved in methylene chloride (12 ml) and treated dropwise with diisopropylcarbodiimide (0.233 ml); the reaction mixture is then stirred overnight at room temperature.

The solvent is removed under vacuum and the dark residue is chromatographed on silica gel eluting with methylene chloride:acetone (85:15).

There are obtained 202 mg of a yellow solid, which is crystallized from CH$_2$Cl$_2$/n-hexane thus affording 245 mg of a white crystalline product, m.p. 167°–169° C.;

Elemental analysis:
calc.: C 68.17%, H 9.53%, N 8.83%, S 6.74%,
found: C 67.70%, H 9.50%, N 8.63%, S 6.52%,
IR (nujol): 3400, 3170, 1655, 1645, 1610, 1530 cm$^{-1}$;
NMR (CDCl$_3$): 6.90.

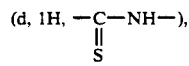

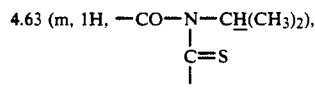

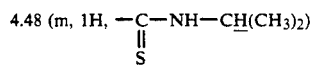

2.99 (dd, 1H, H(5α)), 2.89 (s, 3H, N—CH$_3$), 2.68 (t, 1H, H(17α)); 2.40 (dd, 2H, CH$_2$(2)), 1.25–1.34 (4d, 12H, 4 isopropylic CH$_3$), 0.87 (s, 3H, CH$_3$(19)), 0.79 (s, 3H, CH$_3$(18))

MS (m/z): 475 M$^+$·, 374 M—S=C=N—CH(CH$_3$)$_2$$^{7+}$· 359 374- .CH$_3$$^{7+}$, 316

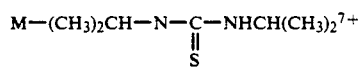

Following analogous procedure the below listed compounds can be prepared:

4-methyl-17β-[N-isopropyl-N-(N-isopropylthiocarbamoyl) carbamoyl]-4-aza-5α-androst-1-en-3-one, 177°–180° C.;

4-methyl-17β-[N-tert-butyl-N-(N-tertbutylthiocarbamoyl) carbamoyl]-4-aza-5α-androstan-3one, m.p. 154°–157° C. dec.;

4-methyl-17β-[N-tert-butyl-N-(N-tert-butylthiocarbamoyl) carbamoyl]-4-aza-5α-androst-1-en-3-one, m.p. 165°–168° C. dec.;

4-methyl-17β-[N-cyclohexyl-N-(N-cyclohexylthiocarbamoyl) carbamoyl]-4-aza-5α-androst-3-one, m.p. 171°–173° C.;

4-methyl-17β-[N-cyclohexyl-N-(N-cyclohexylthiocarbamoyl) carbamoyl]-4-5α-androst-1-en-3-one, m.p. 181°–184° C.;

4-methyl-17β-{N-[3-(dimethylamino)propyl]-N-(N-ethylthiocarbamoyl) carbamoyl}-4-aza-5α-androst-3-one hydrochloride, m.p. 103°–108° C.;

4-methyl-17β-{N-[3-(dimethylamino)propyl]-N-(N-ethylthiocarbamoyl) carbamoyl}-4-aza-5α-androst-1-en-3-one hydrochloride, m.p. 134°–136° C.; and 4-methyl-17β-[N-cyclohexylmethyl-N-(N-cyclohexylmethylcarbamoyl) carbamoyl]-4-aza-5α-androst-3-one, m.p. 156°–159° C.

EXAMPLE 8

17β-[N-isopropyl-N-(N-isopropylthiocarbamoyl)carbamoyl]-4-aza-5α-androst-1-en-3-one S-(2-Pyridyl)4-aza-5α-androst-1-en-3-one-17β-thiocarboxylate (210 mg) is dissolved in methylene chloride (5 ml) and treated with powdered 90% sodium hydrogen sulfide (164.5 mg); then the mixture is stirred at room temperature for 16 hours.

The reaction mixture is poured into 1N HCl (50 ml) and extracted with methylene chloride (4×15 ml); the organic extracts are washed with brine (3×5 ml), water (5 ml) dried over sodium sulphate, and then the solvent is removed under vacuum.

A pale yellow solid (180 mg) is obtained which is washed with diethyl ether (5 ml) to give 165 mg of 4-aza-5α-androst-1-en-3-one-17β-thiocarboxylic acid as a white solid, m.p. 265°–268° C., dec.; IR (nujol): 3180, 2560, 1720, 1690, 1670, 1600 cm$^{-1}$.

4-aza-5α-androst-1-en-3-one-17β-thiocarboxylic acid (153 mg) is dissolved in methylene chloride (25 ml); diisopropylcarbodiimide (0.156 ml) is added and the solution is stirred at room temperature for 3 hours.

After diluting with further 25 ml of methylene chloride, the reaction mixture is washed with 1N sodium hydrogen carbonate (2×5 ml), 1N hydrochloric acid (3×5 ml), brine (3×5 ml), water (5 ml) and then dried over sodium sulphate.

The solvent is removed under vacuum and the white solid material so obtained (230 mg) is purified by flash chromatography (eluant acetone: methylene chloride 50:50) and crystallized from methylene chloride n-hexan to give 105 mg of the title compound, m.p. 204°–206° C. dec;

IR (nujol): 3420, 3280, 3180, 1698, 1665, 1635, 1588, 1520 cm$^{-1}$;

NMR (CDCl$_3$): 7.25

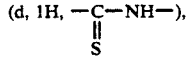

6.80 (d, 1H, H(1)), 5.79 (dd, 1H, H(2)), 5.51 (m, 1H, NH(4)) 4.65

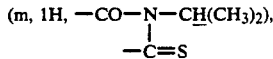

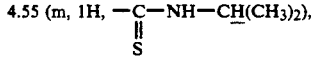

3.30 (dd, 1H, H(5α)), 2.70 (t, 1H, H(17α), 1,40–1,10 (4d, 12H, 4 isopropylic CH$_3$), 0.97 (s, 3H, CH$_3$(19)), 0.85 (s, 3H, CH$_3$(18)).

MS (m/e): 459 M+, 358 M—S=C=N—CH(CH$_3$)$_2$$^{7+}$· 343 390 —CH$_3$$^{7+}$, 272 390- .CO—NH—CH(CH$_3$)$_2$$^{7+}$·

Following analogous procedure, the below listed compounds can be prepared:

17β-[N-isopropyl-N-(N-isopropylthiocarbamoyl)carbamoyl]-4-aza-5α-androstan-3-one, m.p. 179°-181° C.;

17β-[N-tert-butyl-N-(N-tert-butylthiocarbamoyl)carbamoyl]-4-aza-5α-androstan-3-one, m.p. 167°-169° C.;

17β-[N-cyclohexyl-N-(N-cyclohexylthiocarbamoyl)carbamoyl]-4-aza-5α-androstan-3-one, m.p. 183°-185° C.;

17β-{N-[3-(dimethylamino)propyl]-N-(N-ethylthiocarbamoyl) carbamoyl}-4-aza-5α-androstan-3-one hydrochloride, m.p. 139°-140° C.;

17β-[N-tert-butyl-N-(N-tert-butylthiocarbamoyl)carbamoyl]4-aza-5α-androst-1-en-3-one, m.p. 192°-195° C.;

17β-[N-cyclohexyl-N-(N-cyclohexylthiocarbamoyl)carbamoyl]4-aza-5α-androst-1-en-3-one, m.p. 216°-219° C.;

17β-{N-[3-(dimethylamino)propyl]-N-[N-ethylthiocarbamoyl) carbamoyl}-4-aza-5α-androst-1-en-3-one hydrochloride, m.p. 208°-211° C.;

17β-8-[N-cyclohexylmethyl-N-(N-cyclohexylmethylthiocarbamoyl) carbamoyl]-4-aza-5α-androst-1-en-3-one, m.p. 195°-197° C.;

4-methyl-17β-[N-isopropyl-N-(N-isopropylthiocarbamoyl) carbamoyl]-4-aza-5α-androstan-3-one, m.p. 167°-169° C.;

4-methyl-17β-[N-tert-butyl-N-(N-tert-butylthiocarbamoyl) carbamoyl]-4-aza-5α-androstan-3-one, m.p. 154°-157° C. dec.;

4-methyl-17β-[N-cyclohexyl-N-(N-cyclohexylthiocarbamoyl) carbamoyl]-4-aza-5α-androstan-3-one, m.p. 171°-173° C.;

4-methyl-17β-{N-[3-(dimethylamino)propyl]-N-(N-ethylthiocarbamoyl)carbamoyl}-4-aza-5α-androstan-3-one hydrochloride m.p. 103°-108° C.;

4-methyl-17β-[N-cyclohexylmethyl-N-(N-cyclohexylmethylthiocarbamoyl)carbamoyl]-4-aza-5α-androstan-3-one, m.p. 156°-159° C.;

4-methyl-17β-[N-isopropyl-N-(N-isopropylthiocarbamoyl) carbamoyl]-4-aza-5α-androst-1-en-3-one, m.p. 177°-180° C.;

4-methyl-17β-[N-tert-butyl-N-(N-tert-butylthiocarbamoyl) carbamoyl]-4-aza-5α-androst-1-en-3-one, m.p. 165°-168° C. dec.;

4-methyl-17β-[N-cyclohexyl-N-(N-cyclohexylthiocarbamoyl) carbamoyl]-4-aza-5α-androst-1-en-3-one, m.p. 181°-184° C.; and 4-17β-{N-[3-(dimethylamino)propyl]-N-(N-ethylthiocarbamoyl)carbamoyl}-4-aza-5α-androst-1-en-3-one hydrochloride, m.p. 134°-136° C.

EXAMPLE 9

4-methyl-17β-[N-(N-tert-butylcarbamoyl)carbamoyl]-4-aza-5α-androstan-3-one

To a mixture of 4-methyl-4-aza-5α-androstan-3-one 17β-carboxylic acid (100 mg) in anhydrous toluene [2 ml), oxalyl chloride (0.24 ml) is added slowly.

The mixture is stirred at room temperature for 30 min. and then the solvents are removed in vacuo without heating. The residue is dissolved in pyridine (1.36 ml) and then tert-butylurea (35 mg) is added.

After stirring for 2 hours, the reaction mixture is poured into ice water (20 ml) and extracted with methylene chloride. The combined organic extracts are washed with 1N hydrochloric acid, brine, water and dried over sodium sulphate.

Evaporation of the solvent leaves 0.110 g of a dark oil which is chromatographed on silica gel (eluant methylene chloride/acetone 60/40+1% triethylamine) to afford 70 mg of the title compound, m.p. 220°-225° C.;

IR (nujol): 3270, 3220, 3120, 1685, 1640, 1548, 1370 $cm^{-1}$;

NMR (CDCl$_3$): 8.45 (s, 1H, —CO—NH-), 8.11 (s, 1H, —CO—NH-), 3.01 (dd, 1H, 5(α)), 2.90 (s, 3H, N—CH$_3$), 2.19 (t, 1H, CH—CO—NH-), 1.35 (s, 9H, tBu), 0.87 (s, 3H, CH$_3$(19)), 0.79 (s, 3H, CH$_3$(18)).

MS (m/e): 431 M$^+$, 416 M-CH$_3$$^{7+}$.

358 M - H$_2$N—C(CH$_3$)$_3$$^{7+}$.

332 M - OCN—C(CH$_3$)$_3$$^{7+}$.

58 CH(CH$_3$)$_3$$^{7+}$.

Elemental analysis:

Calculated for C$_{25}$H$_{41}$N$_3$O$_3$: C 69.57, H 9.58, N 9.74, found: C 68.47, H 9.43, N 9.39, Following analogous procedure, the below listed compounds can be prepared:

4-methyl-17β-[N-(N-tert-butylcarbamoyl)carbamoyl]-4-aza-5α-androst-1-en-3-one, m.p. 250°-254° C.;

4-methyl-17β-[N-N-butylcarbamoyl)carbamoyl]-4-aza-5α-androstan-3-one, m.p. 142°-146° C.;

4-methyl-17β[N-(N-butylcarbamoyl)carbamoyl]-4-aza-5α-androst-1-en-3-one, m.p. 160°-163° C.

Furthermore, using the appropriate thiourea and following analogous procedure the below listed compounds can also be prepared:

4-methyl-17β-[N-(N-tert-butylthiocarbamoyl)carbamoyl]-4-aza-5α-androstan-3-one, m.p. 183°-185° C. dec.;

4-methyl-17β-[N-(N-tert-butylthiocarbamoyl)carbamoyl]-4-aza-5α-androst-1-en-3-one, m.p. 192°-194° C. dec.;

4-methyl-17β-[N-(N-butylcarbamoyl)carbamoyl]-4-aza-5α-androstan-3-one, m.p. 102°-103° C.; and 4-methyl-17β-[N-(N-butylcarbamoyl)carbamoyl]-4-aza-5α-androst-1-en-3-one, m.p. 108°-111° C.

EXAMPLE 10

4-methyl-17β-{N-isopropyl-(N-methyl-N-isopropylcarbamoyl) carbamoyl)-4-aza-5α-androstan-3-one To a suspension of 4-methyl-17β-{N-isopropyl-N-(N-isopropyl carbamoyl)carbamoyl}-4-aza-5α-androstan-3-one (230 mg) in anhydrous dimethylformamide (5 ml) and methyl iodide (1 ml), kept in a nitrogen atmosphere, sodium hydride (20 mg as a 80% suspension in oil), is added under vigorous stirring.

The suspension is stirred for half an hour at room temperature.

The reaction mixture is poured into ice-water (40 ml) and the precipited product is filtered and crystallized from acetone to give 42 mg of the title compound as a white solid, m.p. 152°-154° C.;

IR (nujol): 1690, 1652, 1632, 1540 cm$^{-1}$;

NMR (CDCl$_3$) : 4.47

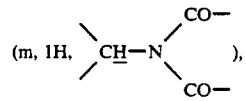

(m, 1H, CH—N(CO—)(CO—) ), 3.97 (m, 1H, —CONH—CH(CH$_3$)$_2$), 2.99 (dd, 1H, H(5α)), 2.97 (s, 3H, N—CH$_3$), 2.69 (t, 1H, —CH—CON<), 2.3 (s, 3H, N—CH$_3$), 1.20-1.33 (4d, 12H, 4 isopropylic CH$_3$), 0.87 (s, 3H, CH$_3$(19)), 0.77 (s, 3H, CH$_3$(18)).

Following analogous procedure also the compound 4-methyl-17β-[N-isopropyl-N-(N-methyl-N-isopropylthiocarbamoyl)carbamoyl]-4-aza-5α-androstan-3-one can be prepared.

EXAMPLE 11

17β-[N-isopropyl-N-(N-isopropylcarbamoyl)carbamoyl]-4-aza-5α-androstan-3-one

Benzyl-17β-{N-isopropyl-N-(N-isopropylcarbamoyl)carbamoyl}-4-aza-5α-androstan-3-one (600 mg) dissolved in glacial acetic acid (10 ml), is hydrogenated under hydrogen pressure (5 psi) in the presence of 10% Pd/C as catalyst (10 W/W) at 60° C. for 6 hours.

The catalyst is filtered off and the solvent is removed in vacuo; the residue is chromatographed on silica gel (eluant methylene chloride/acetone 60/40) to afford 250 mg of white solid that is crystallized from acetone so obtaining 180 mg of the title compound; m.p. 210°–212° C.;

IR (nujol): 3260, 3170, 1690, 1660–1630, 1548 cm$^{-1}$;
NMR(CDCl$_3$) : 6.55 (m, 1H, >NCONH), 6.26 (bs, 1H, CONHCH<), 4.47

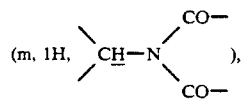

3.97 (m, 1H, —CONH—CH(CH$_3$)$_2$,
3.07 (dd. 1H, H(5α)), 2.69 (t, 1H, —H(17α)), 1.22–1.34 (4d, 12H, 4 isopropylic CH$_3$), 0.89 (s, 3H, CH$_3$(19)), 0.78 (s, 3H, CH$_3$(18)).

Following analogous procedure, the below listed compounds can be prepared:

17β-[N-tert-butyl-N-(N-tert-butylcarbamoyl)carbamoyl]-4-aza-5α-androstan-3-one, m.p. 198°–201° C.;
17β-[N-cyclohexyl-N-(N-cyclohexylcarbamoyl)carbamoyl]-4-aza-5α-androstan-3-one, m.p. 215°–217° C.;
17β-[N-(N-tert-butylcarbamoyl)carbamoyl]-4-aza-5α-androstan-3-one, m.p. 257°–260° C.;
17β-[N-(N-butylcarbamoyl)carbamoyl]-4-aza-5α-androstan-3-one, m.p. 168°–171° C.;
17β-[N-neopentyl-N-(N-ethylcarbamoyl)carbamoyl]-4-aza-5α-androstan-3-one;
17β-{N-[3-(dimethylamino)propyl]-N-(N-ethylcarbamoyl) carbamoyl}-4-aza-5α-androstan-3-one, m.p. 150°–154° C.;
17β-[N-(3-ethoxy-1-propyl)-N-(N-ethylcarbamoyl)carbamoyl]-4-aza-5α-androstan-3-one;
17β-[N-isopropyl-N-(N-isopropylthiocarbamoyl)carbamoyl]-4-aza-5α-androstan-3-one, m.p. 179°–181° C.;
17β-[N-tert-butyl-N-(N-tert-butylthiocarbamoyl)carbamoyl]-4-aza-5α-androstan-3-one, m.p. 167°–169° C.;
17β-[N-cyclohexyl-N-(N-cyclohexylthiocarbamoyl)carbamoyl]-4-aza-5α-androstan-3-one, m.p. 183°–185° C.;
17β-[N-(N-tert-butylthiocarbamoyl)carbamoyl]-4-aza-5α-androstan-3-one, m.p. 197°–198° C.;
17β-[N-(N-butylthiocarbamoyl)carbamoyl]-4-aza-5α-androstan-3-one, m.p. 111°–112° C.;
17β-[N-neopentyl-N-(N-ethylthiocarbamoyl)carbamoyl)-4-aza-5α-androstan-3-one;
17β-{N-[3-(dimethylamino)propyl]-N-(N-ethylthiocarbamoyl) carbamoyl}-4-aza-5α-androstan-3-one, m.p. 139°–140° C.;
17β-[N-(3-ethoxy-1-propyl)-N-(N-ethylthiocarbamoyl) carbamoyl]-4-aza-5α-androstan-3-one.

EXAMPLE 12

17β-[N-isopropyl-N-(N-isopropylcarbamoyl)carbamoyl]-4-aza5α-androst-1-en-3-one

A mixture of 17β-{N-isopropyl-N-[N-isopropylcarbamoyl]carbamoyl}-4-aza-5α-androstan-3-one (306 mg) and benzeneseleninic anhydride (360 mg) in anhydrous diglyme (30 ml), are heated at 120° C. for 14 hours.

The solvent is removed in vacuo and the residue chromatographed on silica gel, eluting with methylene chloride/acetone 60/40, so obtaining 135 mg of the title compound; m.p. 285°–287° C.;

IR (nujol): 3260, 3180, 1690, 1663, 1645, 1600, 1548 cm$^{-1}$;
NMR(CDCl$_3$) : 6.77(d, 1H, H(1)), 6.42(bm, 1H, CONH), 5.80 (dd, 1H, H(2)), 5,47 (bs, 1H, N—H(4)), 4.47

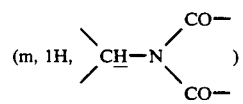

3.97 (m, 1H, —CONHCH<), 3.29 (dd, 1H, H(5α)), 2.69 (t, 1H, —H(17α), 1.36–1.15 (4d, 12H, 4 isopropylic CH$_3$), 0.97 (s, 3H, CH$_3$(19)), 0.74 (s, 3H, CH$_3$(18)).

Following analogous procedures, the below listed compounds can be prepared:

17β-[N-isopropyl-N-(N-methyl-N-isopropylcarbamoyl)carbamoyl]-4-aza-5α-androst-1-en-3-one;
17β-[N-tert-butyl-N-(N-tert-butylcarbamoyl)carbamoyl]-4-aza-5α-androst-1-en-3-one, m.p. 273°–276° C. dec.;
17β-[N-cyclohexyl-N-(N-cyclohexylcarbamoyl)carbamoyl]-4-aza-5α-androst-1-en-3-one, m.p. 290°–292° C.;
17β-[N-(N-tert-butylcarbamoyl)carbamoyl]-4-aza-5α-androst-1-en-3-one, m.p. 300°–305° C. dec.;
17β-[N-(N-butylcarbamoyl)carbamoyl]-4-aza-5α-androst-1-en-3-one, m.p. 242°–245° C.;
17β-[N-neopentyl-N-(N-ethylcarbamoyl)carbamoyl]-4-aza-5α-androst-1-en-3-one;
17β-{N-[3-(dimethylamino)propyl]-N-(N-ethylcarbamoyl) carbamoyl}-4-aza-5α-androst-1-en-3-one hydrochloride, m.p. 220°–224° C.;
17β-[N-(3-ethoxy-1-propyl)-N-(N-ethylcarbamoyl)carbamoyl]-4-aza-5α-androst-1-en-3-one;
17β-[N-isopropyl-N-(N-isopropylthiocarbamoyl)carbamoyl]-4-aza-5α-androst-1-en-3-one, m.p. 204°–206° C.;
17β-[N-isopropyl-N-(N-methyl-N-isopropylthiocarbamoyl) carbamoyl]-4-aza-5α-androst-1-en-3-one;
17β-[N-tert-butyl-N-(N-tert-butylthiocarbamoyl)carbamoyl]-4-aza-5α-androst-1-en-3-one, m.p. 192°–195° C.;
17β-[N-cyclohexyl-N-(N-cyclohexylthiocarbamoyl)carbamoyl]-4-aza-5α-androst-1-en-3-one, m.p. 216°–219° C.;
17β-[N-(N-tert-butylthiocarbamoyl)carbamoyl]-4-aza-5α-androst-1-en-3-one, m.p. 210°–212° C.;

17β-[N-(N-butylthiocarbamoyl)carbamoyl]-4-aza-5α-androst-1-en-3-one, m.p. 133°-135° C.;

17β-[N-neopentyl-N-(N-ethylthiocarbamoyl)carbamoyl]-4-aza-5α-androst-1-en-3-one;

17β-{N-[3-(dimethylamino)propyl]-N-(N-ethylthiocarbamoyl) carbamoyl}-4-aza-5α-androst-1-en-3-one hydrochloride, m.p. 208°-211° C.; and 17β-[N-(3-ethoxy-1-propyl)-N-(N-ethylthiocarbamoyl) carbamoyl]-4-aza-5α-androst-1-en-3-one.

EXAMPLE 13

4-methyl-17β-[N-methyl-N-(N-tert-butylcarbamoyl)-carbamoyl]-4-aza-5α-androstan-3-one To a suspension of 4-methyl-17β-[N-(N-tert-butylcarbamoyl) carbamoyl]-4-aza-5α-androstan-3-one 313 mg) in anhydrous dimethylformamide (5 ml), potassium hydroxide (56 mg) is added and the mixture stirred at room temperature for 30 minutes. Methyl iodide is added dropwise (0.2 ml) and after a further 30 minutes at room temperature, the mixture is heated at 50° C. for 2 hours.

The reaction mixture is poured into ice-water (50 ml) and the precipitated product filtered and crystallized from acetone to give 142 mg of the title compound, m.p. 154°-157° C.;

IR (nujol): 3170, 1690, 1653, 1631, 1540 cm$^{-1}$;
NMR(CDCl$_3$) 6.42 (bm, 1H, CONH), 4.30

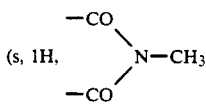

(s, 1H, 2.99 (dd, 1H, H(5α)), 2.97 (s, 3H, N—CH$_3$), 2.69 (t, 1H, —CH—CON<), 1.20-1.33 (s, 9H, t-Butyl), 0.87 (s, 3H, CH$_3$(19) 0.77 (s, 3H, CH$_3$(18)).

Following analogous procedure, starting from 4-methyl-17β-[N-(N-tertbutylthiocarbamoyl)carbamoyl]-4-aza-5α-androstan-3-one, 4-methyl-71β-[N-methyl-N-(N-tert-butylthiocarbamoyl) carbamoyl]4-aza-5α-androstan-3-one was obtained, m.p. 143°-146° C.

EXAMPLE 14

17-cyano-17-hydroxy-4-methyl-4-aza-5α-androstan-3-one 4-methyl-4-aza-5α-androstan-3,17-dione (22.5 g) is dissolved, by heating at 50° C., in freshly distilled acetone cyanohydrin (33 ml); few drops of aqueous 2M Na$_2$CO$_3$ are added and the heating is continued for further 2.5 hours: the cyanohydrin begins to precipitate.

By cooling and then diluting with diisopropyl ether (60 ml added in 3 portions during 24 hours at 0° C.) the title product is precipitated and filtered by suction filtration, washed with diisopropyl ether and dried under vacuum, thus affording 16 g of the title compound, m.p. 154°-157° C.;

IR (nujol): 3320, 2220, 1660 cm$^{-1}$;
NMR (CDCl$_3$): 3.03 (dd, 1H, H(5α)), 2.90 (s, 3H, N—CH$_3$), 2.65 (dd, 2H, CH$_2$(16)), 2.42 (dd, 2H, CH$_2$(2)), 0.92-0.90 (2s, 6H, CH$_3$(18 and 19)).

Following analogous procedure the below listed compound can be prepared:
17-cyano-17-hydroxy-4-aza-5α-androstan-3-one, m.p. 299°-302° C. and 17-cyano-17-hydroxy-4-benzyl-4-aza-5α-androstan-3-one, m.p. 191°-194° C.

EXAMPLE 15

17-cyano-4-methyl-4-aza-5α-androst-16-en-3-one

A mixture of 17-cyano-17-hydroxy-4-methyl-4-aza-5α-androstan-3-one (4.20 g) in pyridine [100 ml) and phosphorous oxychloride (1.5 ml) is heated at 150° C. for 1.5 hours; after cooling, the mixture is poured into ice-water containing concentrated hydrochloric acid (400 ml), the solid precipitated is removed by filtration and purified by flash chromathography (eluant: Benzene/AcOEt/MeOH 85/10/5) thus obtaining 940 mg of solid compound, m.p. 179°-181° C.;

IR (nujol): 2200, 1640, 1580 cm$^{-1}$;
NMR (CDCl$_3$): 6.52 (dd, 1H, H(16)), 3.03 (dd, 1H, H(5α)), 2.90 (s, 3H, N—CH$_3$), 2.42 (dd, 2H, CH$_2$(27), 2.30 and 2.14 (2dd, 2H, CH$_2$(15)), 0.90 (2s, 6H, CH$_3$ (18 and 19)).

Following analogous procedure the below listed compounds can be prepared:
17-cyano-4-aza-5α-androst-16-en-3-one, m.p.>310° C.; and
17-cyano-4-benzyl-4-aza-5α-androst-16-en-3-one, m.p. 247°-250° C.

EXAMPLE 16

4-methyl-4-aza-5α-androst-16-en-3-one-17β-carboxylic acid

A mixture of 17β-cyano-4-methyl-4-aza-5α-androst-16-en-3-one (3.00 g), sodium hydroxide (14 g), methanol (54 ml), and water (48 ml) is heated in a steel vassel, at 180° C. for 3 hours.

The reaction mixture is poured into ice-water and acidified by cautious addition of concentrated sulphuric acid; the precipitate is collected by suction filtration and recrystallized twice from acetone ethyl acetate to afford 1.2 g of the title compound, m.p. 266°-270° C.

Following analogous procedure the below listed compounds can be prepared:
4-aza-5α-androst-16-en-3-one-17β-carboxylic acid, m.p. 287°-291° C.; and
4-benzyl-4-aza-5α-androst-16-en-3-one-17β-carboxylic acid.

EXAMPLE 17

4-methyl-4-aza-5α-androstan-3-one-17β-carboxylic acid

A solution of 4-methyl-4-aza-5α-androst-16-en-3-one-17β-carboxylic acid (300 mg) in 1N sodium hydroxide (600 ml) is hydrogenated at room pressure and temperature in the presence of Nickel-Raney as catalyst.

The catalyst is filtered off and the solution is concentrated at about 100 ml and acidified by cautious addition of concentrated hydrochloric acid.

The precipitate is collected by suction filtration and recrystallized from methylene chloride/methanol to afford 200 mg of the title compound, m.p. 302°-305° C.

Following analogous procedure the below listed compounds can be prepared:
4-aza-5α-androstan-3-one 17β-carboxylic acid, m.p.>310° C.; and
4-benzyl-4-aza-5α-androstan-3-one 17β-carboxylic acid.

EXAMPLE 18

Scored tablets for oral use, each containing 250 mg of the active substance, were manufactured as follows.

| Composition (for 10,000 tablets) | |
| --- | --- |
| 4-methyl-17β-[N-isopropyl-N-(N-isopropylcarbamoyl) carbanoyl]-4-aza-5α-androstan-3-one; | 2500 g |
| corn starch | 275 g |
| talc powder | 187 g |
| calcium stearate | 38 g |

The active substance was granulated with a 4% w/v aqueous solution of methyl cellulose. To the dried granules a mixture of the remainder of the ingredients is added and the final mixture compressed into tablets or proper weight.

EXAMPLE 19

Two-piece hard gelatin capsules for oral use, each containing 250 mg of active substance were manufactured as follows.

| Composition for 10,000 capsules | |
| --- | --- |
| 4-methyl-17β-[N-isopropyl-N-(N-isopropylcarbamoyl) carbamoyl]-4-aza-5α-androstan-3-one; | 2500 g |
| lactose | 1000 g |
| corn starch | 300 g |
| talc powder | 65 g |
| calcium stearate | 35 g |

The active substance was mixed with the starch-lactose mixture followed by the talc and calcium stearate.

The final mixture was encapsulated in the conventional manner.

EXAMPLE 20

Scored tablets for oral use, each containing 250 mg of the active substance, were manufactured as follows.

| Composition (for 10,000 tablets) | |
| --- | --- |
| 4-methyl-17β-[N-isopropyl-N-(N-isopropylthiocarbamoyl) carbamoyl]-4-aza-5α-androstan-3-one; | 2500 g |
| corn starch | 280 g |
| talc powder | 180 g |
| calcium stearate | 40 g |

The active substance was granulated with a 4% w/v aqueous solution of methyl cellulose. To the dried granules a mixture of the remainder of the ingredients is added and the final mixture compressed into tablets of proper weight.

We claim:

1. A compound of the formula (I)

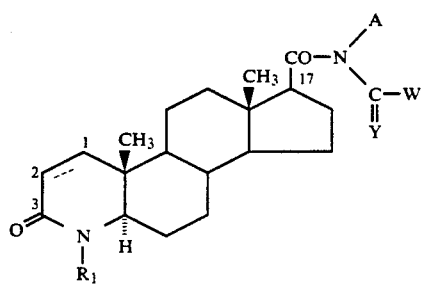

wherein:

$R_1$ is hydrogen, a $C_1$-$C_6$ alkyl group, a benzyl group, a p-methoxy benzyl group, or a benzoyl group;
Y is oxygen or sulphur;
W is a group

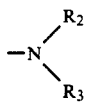

wherein each of $R_2$ and $R_3$ is independently selected from the group consisting of hydrogen, $C_1$-$C_6$ alkyl, $C_5$-$C_6$ cycloalkyl, $C_6$-$C_9$ cycloalkylalkyl and phenyl, wherein each of the groups alkyl, cycloalkyl, cycloalkylalkyl and phenyl may be unsubstituted or substituted with a substituent —$OR_4$ where $R_4$ is hydrogen or $C_1$-$C_4$ alkyl;
A is hydrogen, $C_1$-$C_6$ alkyl, $C_5$-$C_6$ cycloalkyl or $C_6$-$C_9$ cycloalkylalkyl wherein each of the groups alkyl, cycloalkyl and cycloalkylalkyl, may be unsubstituted or substituted with a substituent chosen from:

a) —$OR_4$ wherein $R_4$ is as defined above, and

wherein either each of $R_5$ and $R_6$ is independently selected from the group consisting of hydrogen, $C_1$-$C_6$ alkyl, $C_5$-$C_6$ cycloalkyl and phenyl, or $R_5$ and $R_6$, taken together with the nitrogen atom to which they are linked, are

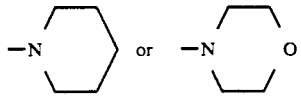

and
the symbol (═) represents a single or a double bond, and the pharmaceutical acceptable salts thereof.

2. A compound of formula (I) according to claim 1 wherein
$R_1$ is hydrogen or $C_1$-$C_6$ alkyl;
Y is oxygen or sulphur;
W is

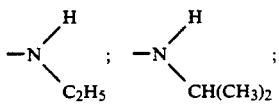

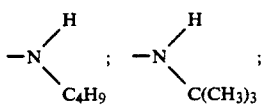

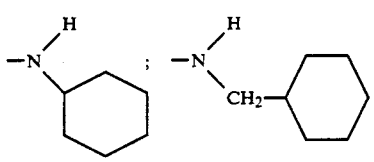

-continued

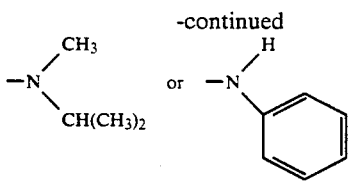

A is hydrogen, methyl, —CH(CH₃)₂, —C(CH₃)₃, —CH₂C(CH₃)₃,

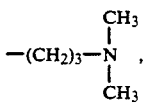

—(CH₂)₃OCH₂CH₃; cylcohexyl; or cyclohexyl methyl;
the symbol $\doteq$ represents a single or double bond, and pharmaceutically acceptable salts thereof.

3. A compound selected from the group consisting of:
4-methyl-17β-[N-isopropyl-N-(N-isopropylcarbamoyl) carbamoyl]-4-aza-5α-androstan-3-one;
4-methyl-17β-[N-isopropyl-N-(N-methyl-N-isopropylcarbamoyl)carbamoyl]-4-aza-5α-androstan-3-one;
17β-[N-isopropyl-N-(N-isopropylcarbamoyl)carbamoyl]-4-aza-5α-androstan-3-one;
4-methyl-17β-[N-isopropyl-N-(N-isopropylcarbamoyl) carbamoyl]-4-aza-5α-androst-1-en-3-one;
17β-[N-isopropyl-N-(N-isopropylcarbamoyl)carbamoyl]-4-aza-5α-androst-1-en-3-one;
17β-[N-isopropyl-N-(N-methyl-N-isopropylcarbamoyl) carbamoyl]-4-aza-5α-androst-1-en-3-one;
4-methyl-17β-[N-tert-butyl-N-(N-tert-butylcarbamoyl) carbamoyl]-4-aza-5α-androstan-3-one;
17β-[N-tert-butyl-N-(N-tert-butylcarbamoyl) carbamoyl]-4-aza-5α-androstan-3-one;
4-methyl-17(-[N-tert-butyl-N-(N-tert-butylcarbamoyl) carbamoyl]-4-aza-5α-androst-1-en-3-one;
17β-[N-tert-butyl-N-(N-tert-butylcarbamoyl)carbamoyl]-4-aza-5α-androst-1-en-3-one;
4-methyl-17β-[N-cyclohexyl-N-[N-cyclohexylcarbamoyl) carbamoyl]-4-aza-5α-androstan-3-one;
17β-[N-cyclohexyl-N-(N-cyclohexylcarbamoyl)carbamoyl]-4-aza-5α-androstan-3-one;
4-methyl-17β-[N-cyclohexyl-N-(N-cyclohexylcarbamoyl) carbamoyl]-4-aza-5α-androst-1-en-3-one;
17β-[N-cyclohexyl-N-(N-cyclohexylcarbamoyl)carbamoyl]-4-aza-5α-androst-1-en-3-one;
4-methyl-17β-[N-[N-tert-butylcarbamoyl)carbamoyl]-4-aza-5α-androstan-3-one;
17β-[N-(N-tert-butylcarbamoyl)carbamoyl]-4-aza-5α-androstan-3-one;
4-methyl-17β-[N-(N-tert-butylcarbamoyl)carbamoyl]-4-aza-5α-androst-1-en-3-one;
17β-[N-(N-tert-butylcarbamoyl)carbamoyl]-4-aza-5α-androst-1-en-3-one;
4-methyl-17β-[N-(N-butylcarbamoyl)carbamoyl]-4-aza-5α-androstan-3-one;
17β-[N-(N-butylcarbamoyl)carbamoyl]-4-aza-5α-androstan-3-one;
4-methyl-17β-[N-(N-butylcarbamoyl)carbamoyl]-4-aza-5α-androst-1-en-3-one;
17β-[N-(N-butylcarbamoyl)carbamoyl]-4-aza-5α-androst-1-en-3-one;
4-methyl-17β-[N-neopentyl-N-(N-ethylcarbamoyl) carbamoyl]-4-aza-5α-androstan-3-one;
17β-[N-neopentyl-N-(N-ethylcarbamoyl)carbamoyl]-4-aza-5α-androstan-3-one;
4-methyl-17β-[N-neopentyl-N-[N-ethylcarbamoyl) carbamoyl]-4-aza-5α-androst-1-en-3-one;
17β-[N-neopentyl-N-(N-ethylcarbamoyl)carbamoyl]4-aza-5α-androst-1-en-3-one;
4-methyl-17β-{N-[3-(dimethylamino)-propyl]-N-(N-ethylcarbamoyl)carbamoyl}-4-aza-5α-androstan-3-one hydrochloride;
17β-{N-[3-(dimethylamino)propyl]-N-(N-ethylcarbamoyl) carbamoyl}-4-aza-5α-androstan-3-one hydrochloride;
4-methyl-17β-{N-[3-(dimethylamino)propyl]-N-(N-ethylcarbamoyl)}carbamoyl-4-aza-5α-androst-1-en-3-one hydrochloride;
17β-{N-[3-(dimethylamino)propyl]-N-(N-ethylcarbamoyl) carbamoyl}-4-aza-5α-androst-1-en-3-one hydrochloride;
4-methyl-17β-[N-(3-ethoxy-propyl)-N-(N-ethylcarbamoyl) carbamoyl]-4-aza-5α-androstan-3-one;
17β-[N-(3-ethoxy-propyl)-N-(N-ethylcarbamoyl)carbamoyl]-4-aza-5α-androstan-3-one;
4-methyl-17β-[N-(3-ethoxy-propyl)-N-(N-ethylcarbamoyl)carbamoyl]-4-aza-5α-androst-1-en-3-one;
17β-[N-(3-ethoxy-1-propyl)-N-(N-ethylcarbamoyl) carbamoyl-]4-aza-5α-androst-1-en-3-one;
4-methyl-17β-[N-cyclohexylmethyl-N-(N-cyclohexylmethylcarbamoyl)carbamoyl]-4-aza-5α-androstan-3-one;
17β-[N-cyclohexylmethyl-N-(N-cyclohexylmethylcarbamoyl) carbamoyl]-4-aza-5α-androst-1-en-3-one;
4-methyl-17β-[N-isopropyl-N-(N-phenylcarbamoyl) carbamoyl]-4-aza-5α-androst-1-en-3-one;
4-methyl-17β-[N-methyl-N-(N-tert-butylcarbamoyl) carbamoyl]-4-aza-5α-androstan-3-one,
and the pharmaceutically acceptable salts thereof.

4. A compound selected from the group consisting of:
4-methyl-17β-[N-isopropyl-N-(N-isopropylthiocarbamoyl) carbamoyl]-4-aza-5α-androstan-3-one;
4-methyl-17β-[N-isopropyl-N-(N-methyl-N-isopropylthiocarbamoyl)carbamoyl]-4-aza-5α-androstan-3-one;
17β-[N-isopropyl-N-(N-isopropylthiocarbamoyl) carbamoyl]-4-aza-5α-androstan-3-one;
4-methyl-17β-[N-isopropyl-N-(N-isopropylthiocarbamoyl) carbamoyl]-4-aza-5α-androst-1-en-3-one;
17β-[N-isopropyl-N-(N-isopropylthiocarbamoyl)carbamoyl]-4-aza-5α-androst-1-en-3-one;
17β-[N-isopropyl-N-(N-methyl-N-isopropylthiocarbamoyl) carbamoyl]-4-aza-5α-androst-1-en-3-one;
4-methyl-17β-[N-tert-butyl-N-(N-tert-butylthiocarbamoyl) carbamoyl]-4-aza-5α-androstan-3-one;
17β-[N-tert-butyl-N-(N-tert-butylthiocarbamoyl) carbamoyl]-4-aza-5α-androstan-3-one;
4-methyl-17β-[N-tert-butyl-N-(N-tert-butylthiocarbamoyl)carbamoyl]-4-aza-5α-androst-1-en-3-one;
17β-[N-tert-butyl-N-(N-tert-butylthiocarbamoyl) carbamoyl]- 4-aza-5α-androst-1-en-3-one;
4-methyl-17β-[N-cyclohexyl-N-(N-cyclohexylthio carbamoyl) carbamoyl]-4-aza-5α-androstan-3-one;
17β-[N-cyclohexyl-N-(N-cyclohexylthiocarbamoyl) carbamoyl]-4-aza-5α-androstan-3-one;
4-methyl-17β-[N-cyclohexyl-N-(N-cyclohexylthiocarbamoyl) carbamoyl]-4-aza-5α-androst-1-en-3-one;
17β-[N-cyclohexyl-N-(N-cyclohexylthiocarbamoyl) carbamoyl]-4-aza-5α-androst-1-en-3-one;
4-methyl-17β-[N-(N-tert-butylthiocarbamoyl) carbamoyl]-4-aza-5α-androstan-3-one;

17β-[N-(N-tert-butylthiocarbamoyl)carbamoyl]-4-aza-5α-androstan-3-one;

4-methyl-17β-[N-(N-tert-butylthiocarbamoyl)carbamoyl-]4-aza-5α-androst-1-en-3-one;

17β-[N-(N-tert-butylthiocarbamoyl)carbamoyl]-4-aza-5α-androst-1-en-3-one;

4-methyl-17β-[N-(N-butylthiocarbamoyl)carbamoyl]-4-aza-5α-androstan-3-one;

17β-[N-(N-butylthiocarbamoyl)carbamoyl]-4-aza-5α-androstan-3-one;

4-methyl-17β-[N-(N-butylthiocarbamoyl)carbamoyl]-4-aza-5α-androst-1-en-3-one;

17β-[N-(N-butylthiocarbamoyl)carbamoyl]-4-aza-5α-androst-1-en-3-one;

4-methyl-17β-[N-neopentyl-N-[N-ethylthiocarbamoyl)carbamoyl]-4-aza-5α-androstan-3-one;

17β-[N-neopentyl-N-[N-ethylthiocarbamoyl)carbamoyl]-4-aza-5α-androstan-3-one;

4-methyl-17β-[N-neopentyl-N-(N-ethylthiocarbamoyl)carbamoyl]-4-aza-5α-androst-1-en-3-one;

17β-[N-neopentyl-N-(N-ethylthiocarbamoyl)carbamoyl]-4-aza-5α-androst-1-en-3-one;

4-methyl-17β-{N-[3-(dimethylamino)-propyl]-N-(N-ethylthiocarbamoyl)carbamoyl}-4-aza-5α-androstan-3-one hydrochloride;

17β-{N-[3-(dimethylamino)propyl]-N-(N-ethylthiocarbamoyl) carbamoyl}-4-aza-5α-androstan-3-one hydrochloride;

4-methyl-17β-{N-[3-(dimethylamino)propyl]-N-(N-ethylthiocarbamoyl)}carbamoyl-4-aza-5α-androst-1-en-3-one, hydrochloride;

17β-{N-[3-(dimethylamino)propyl]-N-(N-ethylthiocarbamoyl}carbamoyl)-4-aza-5α-androst-1-en-3-one hydrochloride;

4-methyl-17β-[N-(3-ethoxy-propyl)-N-(N-ethylthiocarbamoyl) carbamoyl]-4-aza-5α-androstan-3-one;

17β-[N-(3-ethoxy-propyl)-N-(N-ethylthiocarbamoyl)-carbamoyl]-4-aza-5α-androstan-3-one;

4-methyl-17β-[N-(3-ethoxy-propyl)-N-(N-ethylthiocarbamoyl)carbamoyl]-4-aza-5α-androst-1-en-3-one;

17β-[N-(3-ethoxy-1-propyl)-N-(N-ethylthiocarbamoyl) carbamoyl]-4-aza-5α-androst-1-en-3-one;

4-methyl-17β-[N-cyclohexylmethyl-N-(N-cyclohexylmethylthiocarbamoyl)carbamoyl]-4-aza-5α-androstan-3-one;

17β-[N-cyclohexylmethyl-N-(N-cyclohexylmethylthiocarbamoyl) carbamoyl]-4-aza-5α-androst-1-en-3-one;

4-methyl-17β-(N-isopropyl-N-N-phenylthiocarbamoyl) carbamoyl]-4-aza-5α-androst-1-en-3-one;

4-methyl-17β-[N-methyl-N-(N-tert-butylthiocarbamoyl) carbamoyl]-4-aza-5α-androstan-3-one, and the pharmaceutically acceptable salts thereof.

5. The compound 4-methyl-17β-[N-isopropyl-N-(N-isopropylcarbamoyl) carbamoyl]-4-aza-5α-androstan-3-one and the pharmaceutically acceptable salts thereof.

6. A pharmaceutical composition comprising a pharmaceutically acceptable carrier and/or diluent and, as an active principle, an effective amount of a compound of formula (I) according to claim 1 or a pharmaceutically acceptable salt thereof.

7. A method for producing testosterone 5α-reductase inhibition in a patient in need of it, said method comprising administering to the said patient an effective amount of a compound of formula (I) according to claim 1.

* * * * *

UNITED STATES PATENT AND TRADEMARK OFFICE
CERTIFICATE OF CORRECTION

PATENT NO. : 5,155,107
DATED : October 13, 1992
INVENTOR(S) : Achille Panzeri, et. al.

It is certified that error appears in the above-indentified patent and that said Letters Patent is hereby corrected as shown below:

Column 27, line 58, "$C_3$" should read -- $CH_3$ --.
Column 29, line 67, insert -- -aza -- after "4" --.
Column 30, line 67, "390" should read -- 358 --.

Signed and Sealed this

Nineteenth Day of July, 1994

BRUCE LEHMAN

Attest:

Attesting Officer    Commissioner of Patents and Trademarks